US012797541B2

(12) United States Patent
Matsumoto et al.

(10) Patent No.: US 12,797,541 B2
(45) Date of Patent: Nov. 17, 2026

(54) INJECTION DEVICE

(71) Applicant: TAISEI KAKO CO., LTD., Osaka (JP)

(72) Inventors: Ippei Matsumoto, Osaka (JP); Masaya Umezaki, Osaka (JP); Takashi Ogami, Osaka (JP)

(73) Assignee: TAISEI KAKO CO., LTD., Osaka (JP)

( * ) Notice: Subject to any disclaimer, the term of this patent is extended or adjusted under 35 U.S.C. 154(b) by 864 days.

(21) Appl. No.: 17/798,487

(22) PCT Filed: Feb. 12, 2021

(86) PCT No.: PCT/JP2021/005229
§ 371 (c)(1),
(2) Date: Aug. 9, 2022

(87) PCT Pub. No.: WO2021/162086
PCT Pub. Date: Aug. 19, 2021

(65) Prior Publication Data

US 2023/0076297 A1 Mar. 9, 2023

(30) Foreign Application Priority Data

Feb. 14, 2020 (JP) ................................ 2020-023484

(51) Int. Cl.
*A61M 5/20* (2006.01)
*A61M 5/32* (2006.01)

(52) U.S. Cl.
CPC ................ *A61M 5/20* (2013.01); *A61M 5/32* (2013.01)

(58) Field of Classification Search
CPC ........ A61M 5/20; A61M 5/32; A61M 5/2033; A61M 5/31566; A61M 5/3158;
(Continued)

(56) References Cited

U.S. PATENT DOCUMENTS 5,300,030 A 4/1994 Crossman et al.
9,539,392 B2 1/2017 Jennings et al.
(Continued)

FOREIGN PATENT DOCUMENTS

JP 3292747 B2 6/2002
JP 2014-502880 A 2/2014
(Continued)

OTHER PUBLICATIONS

International Search Report for the International application No. PCT/JP2021/005229 mailed on Apr. 27, 2021.
(Continued)

*Primary Examiner* — Jason E Flick
*Assistant Examiner* — Fatimata Sahra Diop
(74) *Attorney, Agent, or Firm* — Ladas & Parry, LLP

(57) ABSTRACT

Provided is an injection device including an engagement releasing mechanism configured to release engagement between a plunger and an engaging member and to cause the plunger to be located at an end point in a manner that the plunger moves from a start point toward the end point by an urging force of a plunger urging portion and the plunger and the engaging member rotate relative to each other around a central axis.

5 Claims, 29 Drawing Sheets

(58) Field of Classification Search

CPC ............ A61M 5/31591; A61M 5/3202; A61M 5/3204; A61M 5/321; A61M 5/3234; A61M 5/50; A61M 2005/31508; A61M 5/31511; A61M 5/3245; A61M 2005/3246; A61M 2005/3252

See application file for complete search history.

(56) References Cited

U.S. PATENT DOCUMENTS

| | | | | |
|---|---|---|---|---|
| 2010/0280460 | A1* | 11/2010 | Markussen | A61M 5/322 604/195 |
| 2012/0184917 | A1* | 7/2012 | Bom | A61M 5/24 604/187 |
| 2013/0267898 | A1 | 10/2013 | Hourmand | |
| 2013/0317479 | A1 | 11/2013 | Brereton et al. | |
| 2014/0336590 | A1 | 11/2014 | Hourmand et al. | |
| 2016/0144129 | A1 | 5/2016 | Mosebach et al. | |
| 2020/0238010 | A1* | 7/2020 | Dugand | A61M 5/3153 |
| 2021/0162133 | A1* | 6/2021 | Dasbach | A61M 5/2033 |

FOREIGN PATENT DOCUMENTS

| | | | |
|---|---|---|---|
| JP | 2014507996 | A | 4/2014 |
| JP | 2015-504713 | A | 2/2015 |
| JP | 2016-523672 | A | 8/2016 |
| JP | 2019-523116 | A | 8/2019 |
| WO | 2013119591 | A | 8/2013 |
| WO | 2013119591 | A1 | 8/2013 |

OTHER PUBLICATIONS

Written Opinion of the International Searching Authority for International application No. PCT/JP2021/005229 mailed on Apr. 27, 2021 with English translation provided by Google Translate.

PCT International Preliminary Report on Patentability (Chapter I) with Written Opinion from PCT/JP2021/005229 mailed on Aug. 25, 2022, and its English translation from WIPO.

First Office Action and search report for Taiwanese Patent Application No. 110105410 issued on Apr. 16, 2024 by the Taiwanese Patent Office.

First Office Action and search report for the corresponding Chinese Patent Application No. 202180013470.X issued by the Chinese Patent Office on Mar. 29, 2024 and its English translation provided by Google Translate.

Extended European Search Report for the corresponding EP patent application No. 21753333.0 issued by the European Patent Office on Feb. 16, 2024.

Office Action in Japanese Patent Application No. 2022-500468, issued on Aug. 9, 2024.

* cited by examiner

INJECTION DEVICE

CROSS-REFERENCE TO RELATED APPLICATIONS

This application is the U.S. national phase of PCT Application No. PCT/JP2021/005229 filed on Feb. 12, 2021, which claims priority to Japanese Patent Application No. 2020-023484 filed on Feb. 14, 2020, the disclosures of which are incorporated herein by reference in their entireties.

FIELD OF THE INVENTION

The present invention relates to an injection device capable of pulling an injection needle out of a housing during use and returning it into the housing after use.

BACKGROUND OF THE INVENTION

As an injector capable of pulling in an injection needle that has come out of a barrel, there is an injector disclosed in Patent Literature 1. The injector includes a front end portion and an intermediate portion that slidably accommodate a capsule with an injection needle in a state where the injection needle protrudes outward and a state where the injection needle is accommodated inside. Further, the injector includes a rear portion formed continuously with the intermediate portion and capable of accommodating a plunger extending rearward from the capsule. In addition, the injector includes: a barrel with an annular rib that separates the intermediate portion and the rear portion; a one-side coil spring that is accommodated in the intermediate portion and urges the capsule toward the annular rib; a drive member that is accommodated in the rear portion and is engaged with a rear end portion of the rod of the plunger; an other-side coil spring that is accommodated in the rear portion and is engaged with the drive member to urge the rod so as to move toward the injection needle; and a cap that is provided in the rear portion and configured to be engaged with the drive member so as not to release urging of the other-side coil spring being in a maximum compressed state and to release the engagement by a predetermined operation. The rear end portion of the rod is bifurcated, and is a bifurcated end portion having a projection at a base and a fitting portion at a distal end. The projection is configured to abut on an inner surface of the capsule when the rod reaches a front end of movement. The drive member includes an annular bottom that is engaged with the fitting portion.

According to the injector, when the cap is operated, the engagement between the cap and the drive member is released, and the drive member moves toward a front end portion by the urging of the other-side coil spring being in the maximum compressed state. Further, when the drive member moves toward the front end portion, the capsule accommodating a distal end side of the rod engaged with the drive member moves by the fitting portion, and the one-side coil spring accommodated in the intermediate portion is compressed toward the front end portion. When the capsule moves toward the front end portion, after the injection needle at the distal end of the capsule protrudes out of the barrel, the rod is pushed by the drive member, and the plunger advances in the capsule. When the plunger reaches the end of movement on the front side, the projection abuts on the inner surface of the capsule, the bifurcated end portion narrows slightly, and the engagement between the annular bottom of the drive member and the fitting portion is released. The one-side coil spring compressed toward the front end portion is released, the urging of the one-side coil spring causes the capsule to move rearward, and thus the injection needle protruding from the distal end of the barrel is pulled in.

CITATION LIST

Patent Literature

Patent Literature 1: JP 3292747 B

However, in the above-described conventional injector, a mechanism for releasing the engagement between the fitting portion of the rod and the annular bottom of the drive member includes a mechanism in which the projection provided at the base of the bifurcated portion abuts on the inner surface of the capsule to narrow the bifurcated end portion. Therefore, due to an error in length or size of the bifurcated end portion or an error in position or size of the projection, the bifurcated end portion may not be narrowed down to the extent that the engagement is released even when the projection abuts on the inner surface of the capsule. Then, even when the injection needle protrudes and the rod reaches the end of movement on the front side, the other-side compressed spring is not released and the capsule does not return, and thus the injection needle does not return, which is dangerous.

SUMMARY OF THE INVENTION

Technical Problem

Therefore, an object of the present invention is to provide an injection device capable of reliably returning an injection needle.

Solution to Problem

An injection device includes: a syringe including a barrel provided with an injection needle at a distal end thereof and a plunger inserted into the barrel so as to be capable of reciprocating between a proximal end side of the barrel as a start point and the injection needle as an end point; a housing formed in a tubular shape to accommodate the syringe, the housing including a barrel accommodating portion formed on one side in a direction of a central axis and accommodating the barrel to be movable between a state where the injection needle is accommodated and a state where the injection needle protrudes from one side of the housing at a predetermined distance from the accommodated state to one side and a plunger accommodating portion formed on the other side relative to the barrel accommodating portion and accommodating the plunger protruding from the proximal end side of the barrel; a barrel urging portion provided in the barrel accommodating portion and urging the barrel from the one side to the other side of the housing; an engaging member disposed in the plunger accommodating portion and engaged with the plunger; a plunger urging portion engaged with the engaging member and urging the plunger from the start point toward the end point; a trigger portion configured to hold urging of the plunger urging portion so as not to release the urging in a state where the barrel accommodates the injection needle by the barrel urging portion and a state where the plunger resists against an urging force of the plunger urging portion and a distal end of the plunger is located at a position of the start point, and to release the holding by performing a predetermined operation, and an engagement releasing mechanism configured to release engagement between the plunger and the engaging member and to cause the plunger to be located at the end point in a manner that the plunger moves from the start point toward the end point by the urging force of the plunger urging portion and the plunger and the engaging member rotate relative to each other around the central axis.

The injection device can be configured such that the engagement releasing mechanism includes a rotary engaging portion provided on the plunger and a rotary engaged portion provided on the barrel, the plunger moves from the start point toward the end point, the rotary engaging portion and the rotary engaged portion are engaged with each other, and thus the plunger rotates around the central axis to release the engagement between the plunger and the engaging member.

The injection device can be configured such that, when the plunger moves from the start point to a position immediately before the end point, the rotary engaging portion and the rotary engaged portion are engaged with each other, and thus the plunger rotates around the central axis to release the engagement between the plunger and the engaging member.

Further, it can be configured such that the plunger urging portion urges the engaging member in a direction in which the engaging member rotates around the central axis; and the engagement releasing mechanism releases the engagement between the plunger and the engaging member by rotating the engaging member around the central axis with respect to the plunger by the urging force of the plunger urging portion.

Further, it can be configured such that the plunger urging portion is a torsion spring, and is configured to rotate the engaging member by an urging force generated by twisting of the torsion spring.

DETAILED DESCRIPTION OF THE PREFERRED EMBODIMENT

Hereinafter, a description will be given on one embodiment of an injection device of the present invention. First, a structure of an injection device 1 of a first embodiment will be described.

Figure 1:
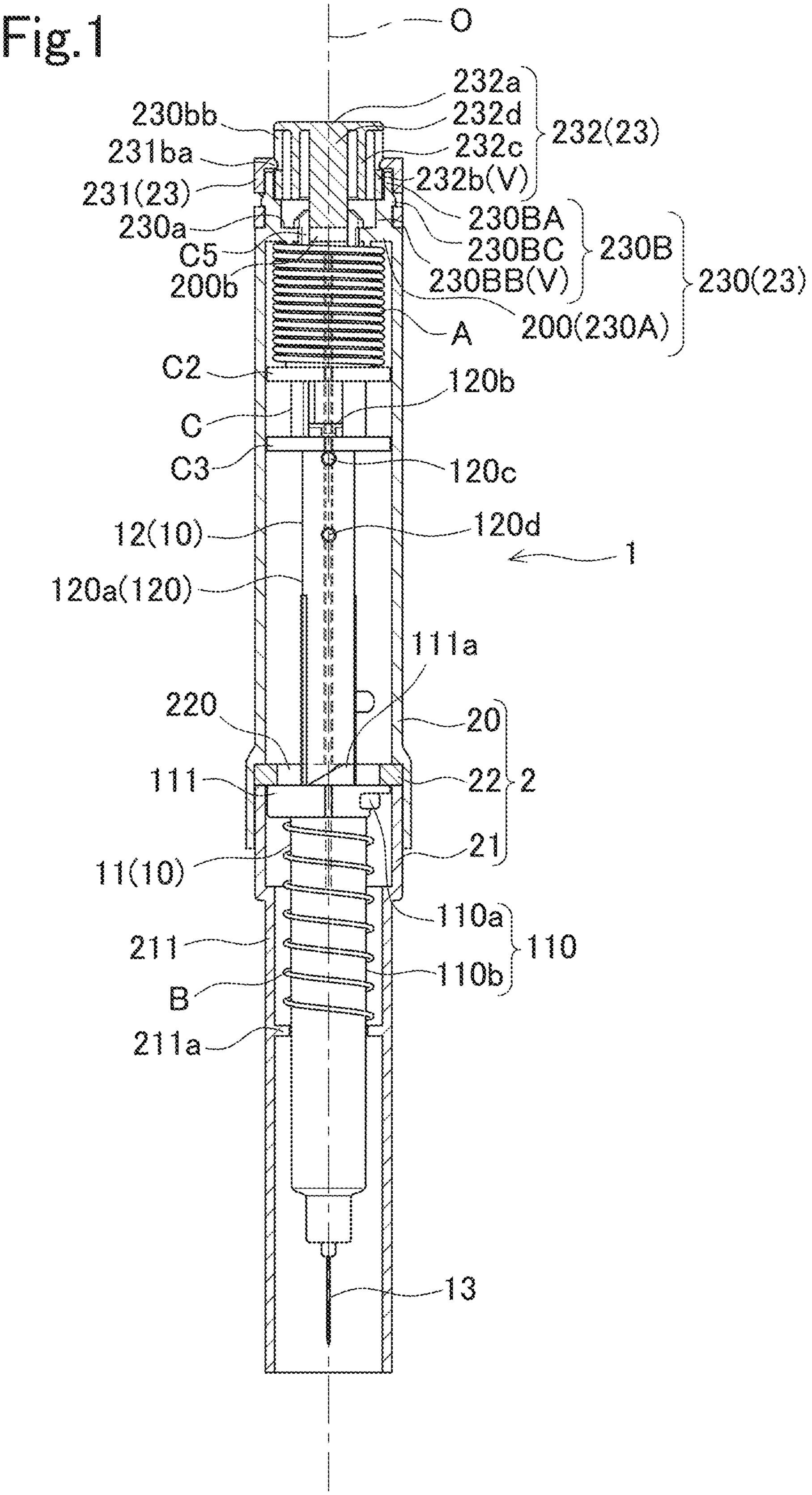
FIG. 1 is a front view of an injection device according to an embodiment of the present invention, in which a housing is shown in a cross section.

The injection device of the present embodiment is used, for example, when a patient administers a drug solution such as an insulin or a rheumatoid therapeutic drug to his/her own body, and is a device in which an injection needle protrudes from the device during injection and the injection needle returns to the inside of the device after injection. As shown in FIG. 1, the injection device 1 of the present embodiment includes a housing 2 extending along a central axis O and accommodating a syringe 10 filled with a drug solution, an engaging member C engaged with a plunger 12 of the syringe 10, a plunger urging portion A engaged with the engaging member C, and a barrel urging portion B engaged with a barrel 11 of the syringe 10. In the following drawings, reference numeral O indicates a central axis, and an upper side is referred to as a "proximal end side" and a lower side is referred to as a "distal end side" in FIG. 1.

FIG. 1 is a front view of the injection device 1 of the present embodiment, in which the housing 2 is taken along the central axis O. The housing 2 is formed to accommodate the syringe 10. Specifically, the housing 2 is formed in a tubular shape to cover the syringe 10. In the present embodiment, the housing 2 is formed in a cylindrical shape. Further, in the present embodiment, the proximal end side in the central axis O is closed by a trigger portion 23 and the distal end side is formed in an opened tubular shape such that the injection needle 13 protrudes out of the device.

The housing 2 includes a partition portion 22 that partitions the inside of the cylinder at a middle part in the central axis O. A barrel accommodating portion 21 is formed on one side of the partition portion 22 of the housing 2 to accommodate the barrel 11. In the barrel accommodating portion 21, the barrel 11 is configured to be movable between a first position in which the barrel abuts on the partition portion 22 and thus the injection needle 13 is accommodated in the housing 2 (see FIGS. 1 and 10) and a second position in which the barrel is separated by a predetermined distance from the partition portion 22 to one side and thus the injection needle 13 protrudes from one side of the housing 2 (see FIG. 12). Further, a plunger accommodating portion 20 is formed on the other side of the partition portion 22 of the housing 2 to accommodate the plunger 12 protruding from the proximal end side of the barrel 11.

The plunger accommodating portion 20 extends from the partition portion 22 toward the proximal end side in the central axis O. As shown in FIG. 1, the plunger accommodating portion 20 accommodates the plunger urging portion A, the engaging member C, and the plunger 12 in order from the proximal end side to the distal end side.

Figure 2:
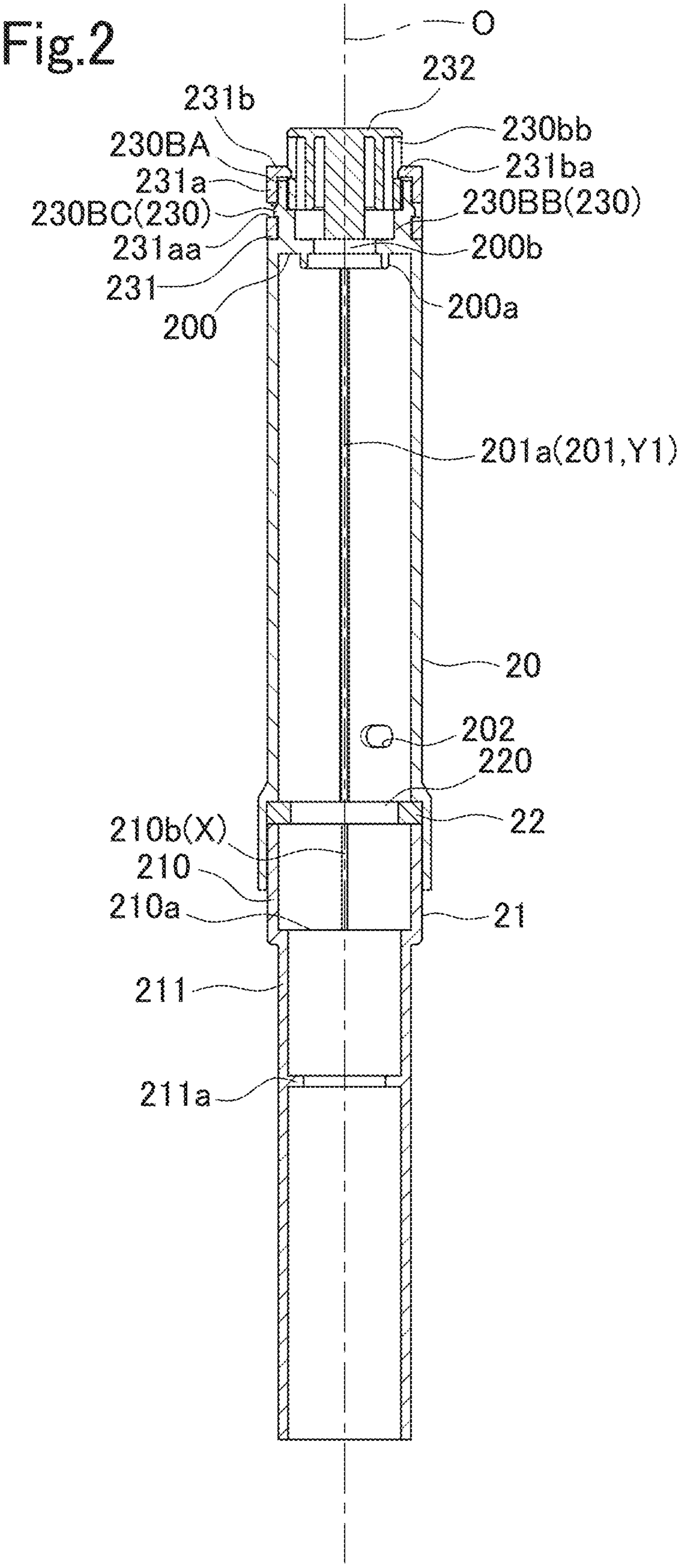
FIG. 2 is a cross-sectional view of the housing according to the embodiment.

As shown in FIG. 2, the plunger accommodating portion 20 includes an urging stand portion 200 (to be described below) that abuts on the plunger urging portion A. The urging stand portion 200 protrudes in a radially inward direction from an inner circumferential surface of the plunger accommodating portion 20 having a cylindrical shape. Further, the urging stand portion 200 is provided with an insertion through-hole 200*b* centered on the central axis O and communicating the inside and the outside of the plunger accommodating portion 20 along the central axis O. Because of this, the urging stand portion 200 is formed in an inner flange shape in the plunger accommodating portion 20. Further, the urging stand portion 200 is provided with a distal end side protrusion portion 200*a* that protrudes toward the distal end side in a direction of the central axis O and prevents the plunger urging portion A from moving in a radial direction. The distal end side protrusion portion 200*a* is inserted into the plunger urging portion A, which will be described below.

The plunger accommodating portion 20 includes an engaging and holding mechanism Y1 that holds the engaging member C so as not to rotate with respect to the plunger accommodating portion 20. In the present embodiment, as shown in FIG. 2, the plunger accommodating portion 20 includes a holding projection portion 201 as the engaging and holding mechanism Y1 on an inner circumferential surface thereof. The holding projection portion 201 protrudes in a radially inward direction from the inner circumferential surface of the plunger accommodating portion 20. The holding projection portion 201 is formed continuously in the direction of the central axis O from the proximal end side to the distal end side of the plunger accommodating portion 20. Further, the holding projection portion 201 includes a plurality of projection portions provided at intervals in a circumferential direction. In the present embodiment, four holding projection portions 201 are provided for every 90° in the plunger accommodating portion having substantially a cylindrical shape. Specifically, the holding projection portion 201 includes a pair of first holding projection portions 201*a* that are fitted into a first holding recess portion C40 (to be described below) in a recess/projection way and a pair of second holding projection portions that are fitted into a second holding recess portion C41 in a recess/projection way. The pair of first holding projection portions 201*a* and the pair of second holding projection portions are disposed to face in a radially inward direction each other on the inner circumferential surface of the plunger accommodating portion 20 having substantially the cylindrical shape. Further, the first holding projection portions 201*a* have a width smaller in the circumferential direction than that of the second holding projection portions. The engaging member C, which will be described below, moves in the direction of the central axis O while being restricted from rotating around the central axis O through the holding projection portion 201. Further, as shown in FIG. 2, both the inside and the outside of the cylinder on the distal end side of the plunger accommodating portion 20 is enlarged in diameter. A proximal end of the partition portion 22 and the barrel accommodating portion 21 are accommodated on the distal end side of the plunger accommodating portion 20.

The plunger accommodating portion 20 is provided with a through hole 202 that penetrates in the radial direction. The through hole 202 is provided along a circumferential surface of the plunger accommodating portion 20 having the cylindrical shape and at a position adjacent to the first holding projection portion 201*a* as shown in FIG. 2. The through hole 202 of the present embodiment includes a pair of through holes provided to face each other in the radial direction.

As shown in FIG. 1, the plunger accommodating portion 20 is engaged with the engaging member C. Further, the plunger urging portion 20 accommodates the plunger urging portion A that urges the plunger 12 from a start point to an end point. In the present embodiment, the start point is located at a position closer to the distal end side than a proximal end of the barrel 11 shown in FIG. 5. In the present embodiment, the end point is a distal end of the barrel 11. Specifically, the plunger urging portion A of the present embodiment is formed by a compression coil spring wound around the central axis O. Further, the engaging member C, which will be described below, is inserted into the plunger urging portion A accommodated in the plunger accommodating portion 20. Then, one end of the plunger urging portion A in the direction of the central axis O abuts on the urging stand portion 200, and the other end thereof abuts on an urging receiving portion C2 of the engaging member C. Because of this, in the present embodiment, the plunger urging portion A is compressed when the engaging member C approaches the urging stand portion 200 in the state shown in FIG. 1.

The housing 2 includes the barrel accommodating portion 21 on the distal end side of the central axis O with the partition portion 22 interposed therebetween. The barrel accommodating portion 21 is formed to be continuous with the plunger accommodating portion 20 through the partition portion 22. The barrel accommodating portion 21 is formed in a tubular shape penetrating in the direction of the central axis O. Because of this, the plunger 12 inserted into the barrel 11 can be extended to the plunger accommodating portion 20 from the proximal end of the barrel accommodating portion 21, and the injection needle 13 can be made to protrude from the distal end of the barrel accommodating portion 21.

As shown in FIG. 2, the barrel accommodating portion 21 is formed in a stepped tubular shape in which an inner diameter and an outer diameter on the proximal end side are larger than an inner diameter and an outer diameter on the distal end side. Therefore, the barrel accommodating portion 21 includes a large cylinder-side barrel accommodating portion 210 having a large inner diameter and outer diameter on the proximal end side and a small cylinder-side barrel accommodating portion 211 that is formed close to the distal end side than the large cylinder-side barrel accommodating portion 210 and has an outer diameter and an inner diameter smaller than those of the large cylinder-side barrel accommodating portion 210. The large cylinder-side barrel accommodating portion 210 includes a barrel receiving portion 210*a* that receives the barrel 11 moved to the distal end side by the urging of the plunger urging portion A and a rotation holding mechanism X that holds a cover portion 111 of the barrel 11 to be described below so as not to rotate with respect to the barrel accommodating portion 21. The barrel receiving portion 210*a* is located at step portion where a proximal end of the small cylinder-side barrel accommodating portion 211 and a distal end of the large cylinder-side barrel accommodating portion 210 are continuous with each other. The barrel receiving portion 210*a* is formed over the entire circumference of the barrel accommodating portion 21. Further, the rotation holding mechanism X is formed in the large cylinder-side barrel accommodating portion 210. Specifically, the rotation holding mechanism X of the present embodiment is continuously formed along the central axis O so as to extend from the partition portion 22 to the barrel receiving portion 210*a* in the large cylinder-side barrel accommodating portion 210. The rotation holding mechanism X of the present embodiment is formed as a holding projection portion 210*b* that is engaged with a holding recess portion 111*b* formed in the cover portion 111 of the barrel 11 to be described below. The holding projection portion 210*b* protrudes inward the barrel accommodating portion 21. In the present embodiment, the holding projection portion 210*b* includes a plurality of holding projection portions provided at intervals in the circumferential direction. Specifically, the holding projection portion 210*b* includes a pair of holding projection portions provided in a direction orthogonal to the central axis O.

The barrel accommodating portion 21 includes an urging stand portion 211*a* on which the barrel urging portion B abuts. As shown in FIG. 1, the urging stand portion 211*a* protrudes inward the small cylinder-side barrel accommodating portion 211 on the distal end side relative to the cover portion 111 (barrel receiving portion 210*a*). The urging stand portion 211*a* protrudes along the inner circumferential surface of the barrel accommodating portion 21. Further, the urging stand portion 211*a* is formed in an inner flange shape along an inner surface of the small cylinder-side barrel accommodating portion 211 such that the barrel 11 can be inserted therethrough.

The partition portion 22 is configured to partition the inside of the housing 2. The partition portion 22 is located between the barrel accommodating portion 21 and the plunger accommodating portion 20. As shown in FIG. 1, the partition portion 22 is a ring-shaped member. The partition portion 22 is configured to protrude in a radially inward direction from the inner surface of the large cylinder-side barrel accommodating portion 210 of the barrel accommodating portion 21 and the inner surface of the plunger accommodating portion 20. Because of this, one surface of the partition portion 22 defines a distal end surface in the plunger accommodating portion 20, and the other surface thereof defines a proximal end surface in the barrel accommodating portion 21. Further, the partition portion 22 includes a through hole 220 through which the plunger 12 penetrates the barrel accommodating portion 21 and the plunger accommodating portion 20. The through hole 220 is formed smaller than the barrel accommodating portion 21 and the plunger accommodating portion 20. Further, the partition portion 22 of the present embodiment is formed in an inner flange shape in the housing 2. Because of this, as shown in FIG. 1, the partition portion 22 can come into contact with the proximal end surface of the barrel 11 in the barrel accommodating portion 21. Therefore, the partition portion 22 restricts the proximal end side of the barrel 11 from moving.

The barrel urging portion B urges the barrel 11 from one side of the housing 2 toward the partition portion 22. The barrel urging portion B is disposed in the barrel accommodating portion 21. The barrel urging portion B of the present embodiment is formed by a compression coil spring wound around the central axis O. Specifically, as shown in FIG. 1, the barrel urging portion B is a coil spring through which the barrel 11 can be inserted. Further, the barrel urging portion B has one end side abutting on the barrel 11 and the other side abutting on the urging stand portion 211*a* in the direction of the central axis O. Specifically, one end side of the barrel urging portion B abuts on the side surface on the distal end side of the cover portion 111 of the barrel 11. Because of this, when the barrel 11 moves away from the partition portion 22 to the distal end side of the barrel accommodating portion 21, the barrel urging portion B is compressed between the barrel 11 and the urging stand portion 211*a*. Therefore, the barrel urging portion B urges the barrel 11 toward the partition portion 22 (toward the proximal end side). An urging force of the barrel urging portion B of the present embodiment is set to be weaker than an urging force of the plunger urging portion A.

The injection device 1 of the present embodiment includes a trigger portion 23 configured to release the urging of the plunger urging portion A. The trigger portion 23 is configured to lock the urging of the plunger urging portion A so as not to release the urging in a state where the barrel 11 abuts on the partition portion 22 by the urging force of the barrel urging portion B, the plunger 12 resists against the urging force of the plunger urging portion A, and the distal end of the plunger 12 is located at a position of a start point. In other words, the trigger portion 23 has an urging force holding position at which the urging force of the plunger urging portion A is held so as not be released. The trigger portion 23 releases the lock by a predetermined operation. In other words, the trigger portion 23 moves from the urging force holding position to the urging force releasing position by a predetermined operation. As shown in FIG. 1, the trigger portion 23 includes a trigger attaching portion 230 provided at the proximal end of the plunger accommodating portion 20, a trigger body portion 232 operated by a user, and a trigger lock operation portion 231 that lock the trigger body portion 232 so as not to be operated by the user 231. The trigger attaching portion 230 is provided at the proximal end of the plunger accommodating portion 20. The trigger attaching portion 230 includes a proximal end portion 230A of the plunger accommodating portion 20 and a circular cylinder portion 230B protruding from the proximal end portion 230A toward the proximal end side in the direction of the central axis O.

The insertion through-hole 200*b* centered on the central axis O is formed in the proximal end portion 230A. Further, the proximal end portion 230A includes a hooking portion 230*a* locked with the trigger locking portion C5 of the engaging member C, a side surface of which on the proximal end side is inserted through the insertion through-hole 200*b*. In the present embodiment, the proximal end portion 230A is also the urging stand portion 200.

The circular cylinder portion 230B is formed around the central axis O and has a cylindrical shape. The circular cylinder portion 230B includes a circular cylinder body portion 230BA provided to surround the hooking portion 230*a*, a lock step portion 230BB protruding in the radially inward direction from an inner surface of the circular cylinder body portion 230BA, and a projection portion 230BC protruding in a radially outward direction from an outer surface of the circular cylinder body portion 230BA. The lock step portion 230BB is a step portion that restricts an operation of the trigger body portion 232. Specifically, the lock step portion 230BB restricts the trigger body portion 232 from moving toward the distal end side such that the trigger body portion 232 (outer skirt portion 232*b*) cannot be pushed toward the distal end side in an initial state (state before operation) of FIGS. 1 and 10.

The projection portion 230BC guides a rotation operation of the trigger lock operation portion 231. The lock step portion 230BB and the projection portion 230BC also include a pair of lock step portions and a pair of projection portions so as to face each other in a radial direction of the circular cylinder body portion 230BA, respectively.

The trigger body portion 232 is pushed by the user of the injection device 1 from the proximal end side to the distal end side in the direction of the central axis O to activate an injection action of the injection device 1. The trigger body portion 232 includes a top plate portion 232*a* that is pressed by the user who operates, an outer skirt portion 232*b* that is suspended from an outer peripheral edge of the top plate portion 232*a* toward the distal end side, an inner skirt portion 232*c* that is suspended from the top plate portion 232*a* inside the outer skirt portion 232*b*, and a flat plate portion 232*d* that is suspended from the top plate portion 232*a* inside the inner skirt portion 232*c*. The top plate portion 232*a* has a disk shape centered on the central axis O. A surface of the top plate portion 232*a* on the proximal end side is a flat surface such that the user can easily press.

The outer skirt portion 232*b* is formed in a cylindrical shape over the entire circumference around the central axis O. As shown in FIG. 1, the outer skirt portion 232*b* is configured such that the distal end portion thereof abuts on the lock step portion 230BB of the trigger attaching portion 230. In other words, the distal end portion of the outer skirt portion 232*b* and the lock step portion 230BB form a lock mechanism portion V for locking the operation of the trigger portion 23.

Figure 12:
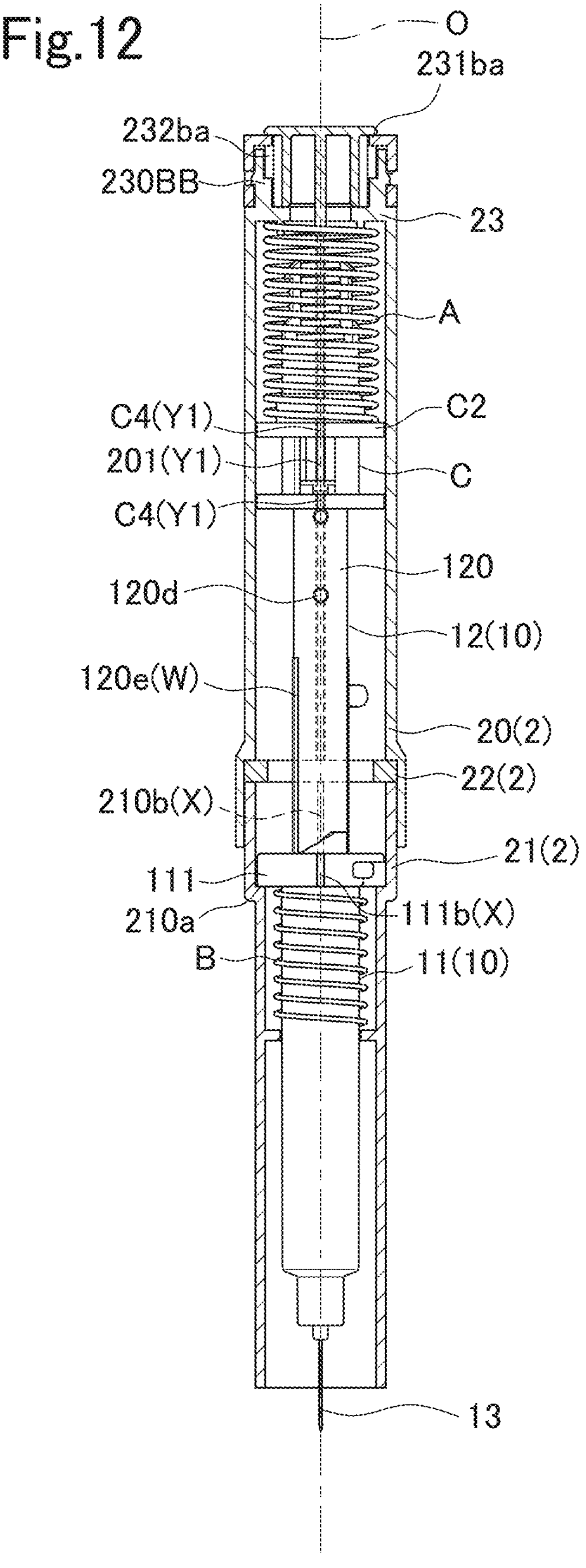
FIG. 12 is a view showing the injection device of the embodiment, in which a housing is shown in a cross section and an injection needle is pulled out of the housing.

As shown in FIG. 12, the outer skirt portion 232*b* is formed with a release groove 232*ba* that is opened at the distal end portion of the outer skirt portion 232*b*. The release groove 232*ba* is formed in the direction of the central axis O. Further, the release groove 232*ba* is configured such that lock step portion 230BB can be inserted therethrough. Therefore, when positions in the circumferential direction of the release groove 232*ba* and the lock step portion 230BB coincide with each other, the lock by the lock mechanism portion V is released as shown in FIG. 12. Therefore, the pushing operation can be made for the trigger body portion 232.

As shown in FIG. 1, the outer skirt portion 232*b* is formed with an interlocking groove 230*bb* that is closed at the distal end portion of the outer skirt portion 232*b*. The interlocking groove 230*bb* is formed in the direction of the central axis O. Further, the interlocking groove 230*bb* is fitted with an interlocking projection portion 231*ba* of the trigger lock operation portion 231. Thus, the trigger body portion 232 and the trigger lock operation portion 231 interlock with each other in rotation around the central axis O.

The inner skirt portion 232*c* is formed in a cylindrical shape over the entire circumference around the central axis O. An inner diameter of the inner skirt portion 232*c* is substantially equal to an inner diameter of the insertion through-hole 200*b* at the proximal end. When the trigger body portion 232 is pushed, the inner skirt portion 232*c* is pushed so as to abut on the hooking portion 230*a* of the proximal end portion 230A. Thus, the lock of the trigger locking portion C5 described below, which is locked to the hooking portion 230*a*, is released. In other words, the inner skirt portion 232*c* functions as a trigger activation portion for activating the injection action.

The flat plate portion 232*d* has a length in the direction of the central axis O, and is formed in a plate shape having a width and a thickness in a direction orthogonal to the length. The flat plate portion 232*d* is longer than the outer skirt portion 232*b* and the inner skirt portion 232*c*. Further, the flat plate portion 232*d* has a width substantially equal to the width between a pair of trigger locking portions C5.

The trigger lock operation portion 231 is a member that is operated to release the lock of the trigger portion 23 in the locked state. As shown in FIG. 2, the trigger lock operation portion 231 includes a circular cylinder body portion 231*a* formed around the central axis O and an inner flange portion 231*b* extending in a radially inward direction from a proximal end in the direction of the central axis O of the circular cylinder body portion 231*a*. The circular cylinder body portion 231*a* is configured to rotatably surround the periphery of the trigger attaching portion 230.

The circular cylinder body portion 231*a* is formed with a rotating groove 231*aa* extending in the circumferential direction. The rotating groove 231*aa* is formed such that the projection portion 230BC of the trigger attaching portion 230 can be fitted thereinto. Both ends in the circumferential direction of the rotating groove 231*aa* abut on the projection portion 230BC, and thus a rotating angle of the trigger lock operation portion 231 is defined.

The inner flange portion 231*b* is formed over the entire circumference of the circular cylinder body portion 231*a*. The inner flange portion 231*b* includes an interlocking projection portion 231*ba* protruding in the radially inward direction at an inner circumferential end. The interlocking projection portion 231*ba* is fitted into the interlocking groove 230*bb*. Thus, the trigger lock operation portion 231 and the trigger body portion 232 rotate together. In the present embodiment, the interlocking projection portion 231*ba* includes a plurality of interlocking projection portions. As shown in FIG. 12, the interlocking projection portion 231*ba* is also fitted into the release groove 232*ba*.

In such a trigger portion 23, the trigger body portion 232 is installed inside the trigger attaching portion 230. The trigger lock operation portion 231 is installed outside the trigger attaching portion 230 so as to interlock with the trigger body portion 232. Specifically, as shown in FIG. 1, the distal end portion of the outer skirt portion 232*b* in the trigger body portion 232 abuts on the lock step portion 230BB in an initial state (lock state before use). Further, the inner skirt portion 232*c* is separated from hooking portion 230*a* toward the proximal end side in the direction of the central axis O. The flat plate portion 232*d* is inserted between the pair of trigger locking portions C5 in a posture in which a width direction thereof is conformed to the direction in which the pair of trigger locking portions C5 face each other. In the present embodiment, the trigger body portion is disposed with respect to the trigger attaching portion 230 as described above.

In the trigger lock operation portion 231, as shown in FIG. 2, the circular cylinder body portion 231*a* surrounds the outside of the circular cylinder body portion 230BA. Further, the projection portion 230BC is fitted into the rotating groove 231*aa*. The interlocking projection portion 231*ba* is fitted into the interlocking groove 230*bb* and the release groove 232*ba*. In this way, the trigger lock operation portion 231 is disposed with respect to the trigger attaching portion 230. When the trigger lock operation portion 231 rotates, the trigger body portion 232 rotates in conjunction therewith. Then, when the release groove 232*ba* rotates until it coincides with the lock step portion 230BB in the circumferential direction, the lock of the lock mechanism portion V is released. Specifically, the lock of the lock mechanism portion V means that the distal end portion of the outer skirt portion 232*b* abuts on the lock step portion 230BB. Thus, the pushing operation can be made for the trigger body portion 232 (see FIG. 12). At this time, the flat plate portion 232*d* has a thickness direction that is conformed to the direction in which the pair of trigger locking portions C5 face each other, and allows the pair of trigger locking portions C5 to bend toward the radially inner side.

When the trigger body portion 232 is pushed, the inner skirt portion 232*c* (trigger activation portion) approaches the hooking portion 230*a*. The inner skirt portion 232*c* abuts on the trigger locking portion C5 locked to the hooking portion 230*a*, and allows the trigger locking portion C5 to bend toward the radially inner side. Accordingly, the lock between the hooking portion 230*a* and the trigger locking portion C5 is released. Thus, the injection action of the injection device 1 is activated.

As shown in FIG. 1, the syringe 10 includes the barrel 11 provided with the injection needle 13 at the distal end thereof and the plunger 12 inserted into the barrel 11 so as to be capable of reciprocating between the proximal end side of the barrel 11 as a start point and the injection needle 13 as an end point. In the present embodiment, the barrel 11 is accommodated in the barrel accommodating portion 21. Further, the barrel 11 includes a barrel body 110 filled with a drug solution and a cover portion 111 attached to the barrel body 110. Further, the barrel body 110 of the present embodiment includes a body portion 110*b* having a cylindrical shape and an outer flange portion 110*a* protruding in a radially outward direction from the proximal end of the body portion 110*b*. The cover portion 111 is attached to the barrel body 110 to cover the outer flange portion 110*a* of the barrel body 110. Specifically, the cover portion 111 is formed in a tubular shape in which a part of an outer circumferential surface is cut and a bottom surface is formed in a C-shape. The cover portion 111 of the present embodiment is formed to be larger than the outer flange of the barrel body 110 in the radial direction. Because of this, the outer flange portion 110*a* of the barrel body 110 is inserted slidingly from the side surface of the cover portion 111 such that the C-shaped bottom surface holds the barrel body 110 having a tubular shape. Thus, the cover portion 111 is attached to the barrel body 110.

Figure 3:
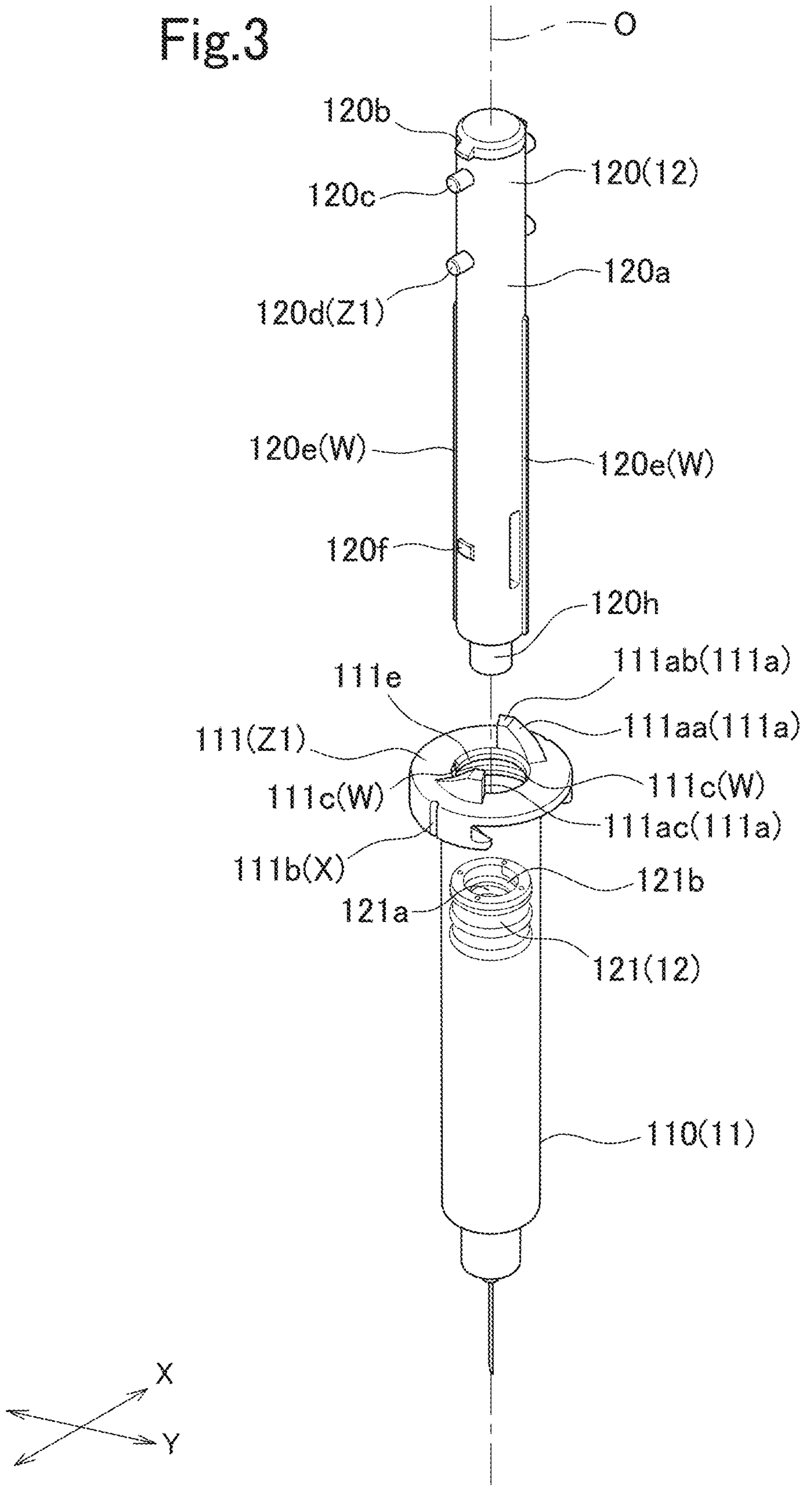
FIG. 3 is an exploded perspective view of a syringe of the embodiment.

As shown in FIG. 3, the cover portion 111 is formed with an insertion through-hole 111*e* through which the plunger 12 is inserted into the barrel 11. The insertion through-hole 111*e* is provided in a circular shape in an upper surface of the cover portion 111. Further, the insertion through-hole 111*e* is formed so as to be continuous with an opening of the barrel body 110 having a tubular shape when the cover portion 111 is attached to the barrel body 110. The insertion through-hole 111*e* of the present embodiment is formed to be larger than a rod 120 to be described below and smaller than the opening of the barrel body 110.

As shown in FIGS. 1 and 3, the barrel 11 is provided with a rotary engaged portion 111*a*. The rotary engaged portion 111*a* engages with a rotary engaging portion 120*d* to be described below when the plunger 12 moves from the start point to a position immediately before reaching the end point as will be described below. Therefore, the rotary engaged portion 111*a* is configured to rotate the plunger 12 around the central axis O. Specifically, the rotary engaged portion 111*a* is an inclined portion 111*a* including an inclined surface 111*aa* that guides the plunger 12 to rotate around the central axis O, a horizontal surface 111*ab* extending in a horizontal direction from the inclined surface 111*aa*, and a vertical surface 111*ac* extending in the direction of the central axis O from the horizontal surface 111*ab*. The inclined surface 111*aa* of the inclined portion 111*a* is disposed on the upper surface of the cover portion 111 attached to the barrel body 110 as shown in FIG. 3. The inclined surface 111*aa* is inclined so as to slide when the rotary engaging portion 120*d* is engaged. The inclined surface 111*aa* is a surface on which the rotary engaging portion 120*d* approaching from the proximal end side in the direction of the central axis O abuts. The inclined surface 111*aa* is a spiral inclined surface 111*aa* that turns around the central axis O and is inclined toward the distal end side of the central axis O. Further, a distance between the horizontal surface 111*ab* and the upper surface of the cover portion 111 is substantially equal to the distance between the distal end surface and the proximal end surface of the partition portion 22. Further, as shown in FIG. 3, the inclined portion 111*a* is formed around the insertion through-hole 111*e* that is formed in the circular shape in the cover portion 111. Further, the inclined portion 111*a* is formed so as to enter the through hole 220 of the partition portion 22 when the barrel 11 abuts on the partition portion 22. In the present embodiment, the inclined portion 111*a* functions as an engagement releasing mechanism Z1 that releases the engagement between the plunger 12 and the engaging member C. In the present embodiment, a pair of inclined portions 111*a* are formed along the circular insertion through-hole 111*e*.

As shown in FIG. 3, the cover portion 111 includes the holding recess portion 111*b* as a rotation holding mechanism X that holds the rotary engaged portion 111*a* so as not to rotate with respect to the barrel accommodating portion 21. Further, the cover portion 111 includes a rotation restriction portion W that restricts the plunger 12 from rotating around the central axis O up to a predetermined distance in the direction of the central axis O when the plunger 12 is inserted into the barrel 11. In the present embodiment, the cover portion 111 includes an axial movement groove portion 111*c* as the rotation restriction portion W. The holding recess portion 111*b* is formed in the direction along the central axis O on the outer circumferential surface of the cover portion 111 formed in a circular shape in a plan view. In the present embodiment, a pair of holding recess portions 111*b* are formed in an X direction shown in FIG. 4 in the radial direction of the cover portion 111 orthogonal to the direction of the central axis O.

As shown in FIG. 3, the axial movement groove portion 111*c* is formed in the direction of the central axis O so as to cut out the inner circumferential surface of the insertion through-hole 111*e*, and an axial movement protrusion portion 120*e* (which will be described below) of the rod 120 is inserted into the axial movement groove portion 111*c*. In the present embodiment, two axial movement groove portions 111*c* are formed in the cover portion 111.

Figure 5:
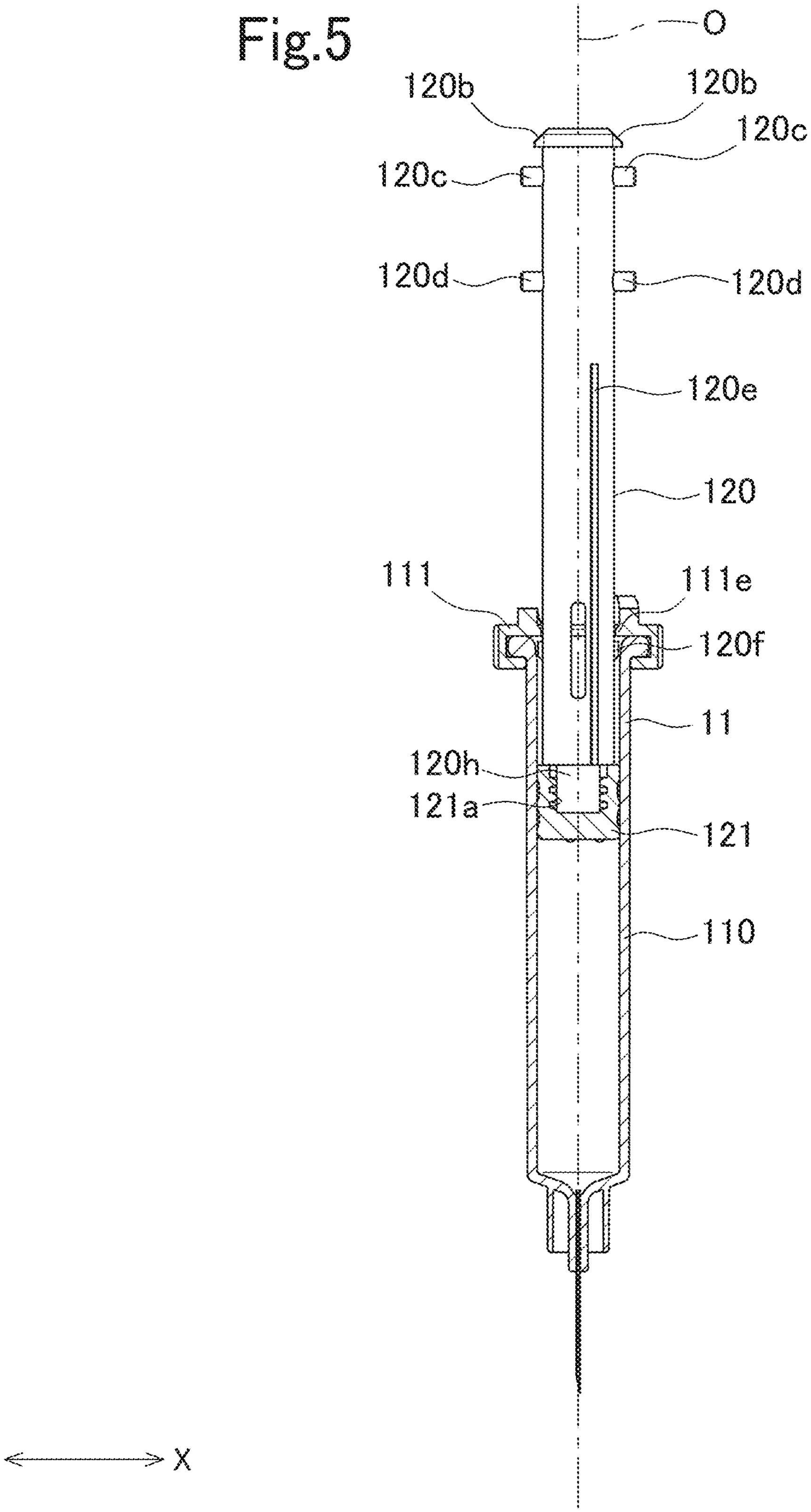
FIG. 5 is a right side view of the syringe of the injection device of the embodiment, in which a barrel and a piston are shown in a cross section.

As shown in FIG. 1, the plunger 12 includes a piston 121 (not shown in FIG. 1) that reciprocates between the start point and the end point in a state of being in close contact with the inside of the barrel 11 in a liquid tight manner and a rod 120 that is engaged with the piston 121. In order to prevent the drug solution from leaking to the outside of the barrel 11, the piston 121 is disposed to seal the inside of the barrel 11 as shown in FIGS. 3 and 5. Further, the piston 121 is engaged with the rod 120 which will be described below. Specifically, the piston 121 includes a coupling hole 121*a* into which a distal end protrusion portion 120*h* of the rod 120 is inserted and an annular protrusion 121*b* having a spiral shape formed in the coupling hole 121*a* along a circumferential surface as shown in FIG. 5. In the present embodiment, since the piston 121 is larger than the insertion through-hole 111*e* provided in the cover portion 111, there is no possibility that the piston 121 will fall out of the inside of the barrel 11.

As shown in FIG. 1, the rod 120 is formed to extend in the housing 2 along the central axis O. One side (distal end side) of the rod 120 in the direction of the central axis O is engaged with the piston 121 (not shown in FIG. 1) in the barrel 11, and the other side (proximal end side) thereof is engaged with the engaging member C. As shown in FIG. 3, the rod 120 includes a rod body 120*a* extending in the direction of the central axis O, a pin portion 120*b* provided on the rod body 120*a*, a first branch portion 120*c* engaged with the engaging member C, a second branch portion 120*d* that allows the plunger 12 to rotate, an axial movement protrusion portion 120*e* that prevents the plunger 12 from rotating around the central axis O, a fall-off proof portion 120*f* that prevents the plunger 12 from falling off the barrel 11, and a distal end protrusion portion 120*h* to be inserted into the piston 121. The rod body 120*a* is formed in a columnar shape. The rod body 120*a* is formed to have substantially the same size in the radial direction as the insertion through-hole 111*e* formed in the cover portion 111. In the present embodiment, the rod body 120*a* is formed to be larger than the barrel body 110 of the barrel 11 in the direction of the central axis O such that the proximal end side of the plunger 12 extends out of the barrel 11 when the plunger 12 is inserted up to the end point.

Figure 4:
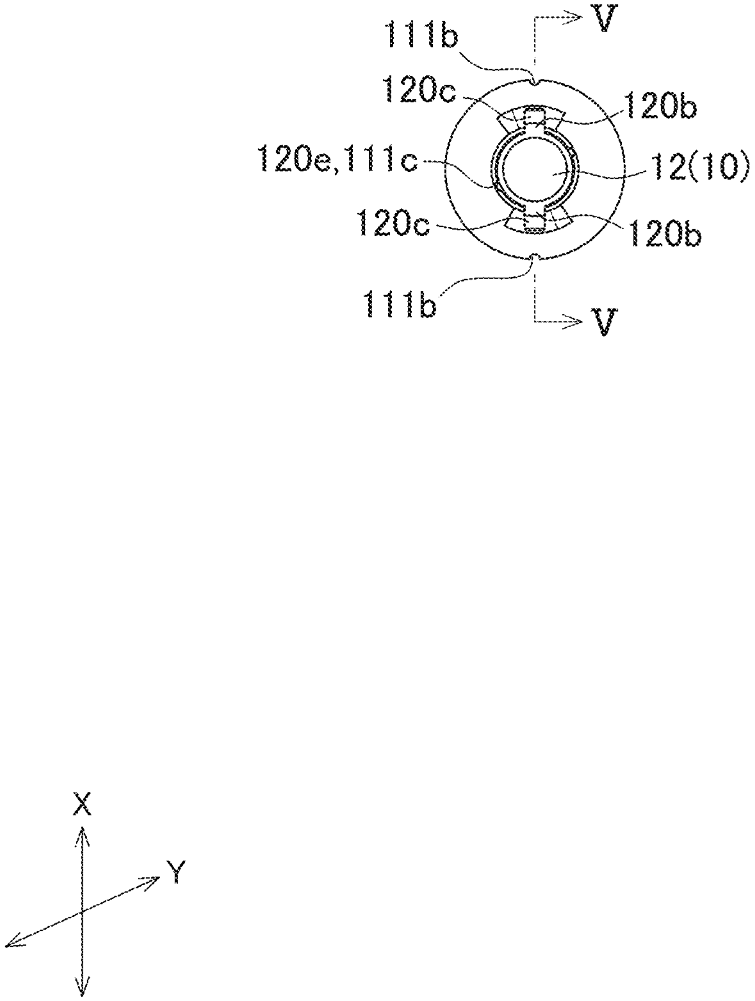
FIG. 4 is a plan view of the syringe of the embodiment.

The pin portion 120*b* provided on the rod body 120*a* engages the plunger 12 with the engaging member C. Specifically, in the injection device 1 shown in FIG. 1, the pin portion 120*b* is inserted into a release hole C30 (not shown in FIG. 1) of the engaging member C. Further, the pin portion 120*b* is disposed at a position that does not coincide with that of the release hole C30 in the circumferential direction. Thus, the plunger 12 is prevented from falling off the engaging member C, and the engagement between the engaging member C and the plunger 12 is maintained. In the present embodiment, the pin portion 120*b* is formed to protrude from the proximal end of the rod body 120*a* in the direction (specifically, X direction) orthogonal to the central axis O as shown in FIG. 3. In the present embodiment, the pin portion 120*b* functions as a rotation-prevention fitting portion 120*b* that fits with a rotation-prevention fitted portion C20 which will be described below. Further, when the plunger 12 is inserted into the barrel 11 and the syringe 10 is formed, the pin portion 120*b* includes a pair of pin portions disposed to face each other in the X direction as shown in FIGS. 4 and 5.

As shown in FIG. 3, the first branch portion 120*c* protrudes from an outer circumferential surface of the rod body 120*a* having a columnar shape. The first branch portion 120*c* is provided on the proximal end side of the rod body 120*a* in the direction of the central axis O. Further, the first branch portion 120*c* is disposed on the distal end relative to the pin portion 120*b*. Specifically, as shown in FIG. 1, when the pin portion 120*b* at the proximal end of the plunger 12 is inserted into the engaging member C and engaged therewith, the first branch portion 120*c* abuts on an urging engaging portion C3 of the engaging member C such that the engaging portion C is sandwiched between the first branch portion 120*c* and the pin portion 120*b*. Thus, the plunger 12 engages with the engaging member C. Because of this, the first branch portion 120*c* of the present embodiment functions as an urging engaged portion 120*c* that engages with the urging engaging portion C3. Further, as shown in FIG. 1, the first branch portion 120*c* is located on the bottom surface side (distal end side) of the engaging member C, and restricts the plunger 12 from moving toward the engaging member C. In the present embodiment, the first branch portion 120*c* includes a pair of first branch portions provided in the X direction as shown in FIGS. 4 and 5.

As shown in FIG. 3, the second branch portion 120*d* is provided on the distal end side in the direction of the central axis O relative to the first branch portion 120*c*. The second branch portion 120*d* is the rotary engaging portion 120*d* provided on the plunger 12. The second branch portion 120*d* functions as the engagement releasing mechanism Z1 that releases the engagement between the plunger 12 and the engaging member C. The second branch portion 120*d* engages with the inclined portion (rotary engaged portion) 111*a* provided on the cover portion 111 when the plunger 12 moves from the position (start point) closer to the distal end side than the proximal end of the barrel 11 to the position immediately before reaching the distal end (end point) of the barrel 11. Thus, the rod 120 rotates around the central axis O. Because of this, when the plunger 12 and the barrel 11 are coupled to form the syringe 10, the second branch portion 120*d* is disposed to face the inclined portion 111*a* in the direction of the central axis O. Further, the second branch portion 120*d* of the present embodiment is formed in a circular protrusion shape to easily rotate along the inclined portion 111*a*. Further, the second branch portion 120*d* includes a pair of second branch portions provided in the X direction as shown in FIGS. 4 and 5.

The axial movement protrusion portion 120*e* functions as the rotation restriction portion W that restricts the plunger 12 inserted into the barrel 11 so as not to rotate around the central axis O. Specifically, the axial movement protrusion portion 120*e* is inserted into the barrel 11 along the axial movement groove portion 111*c* provided in the cover portion 111. This restricts the rod 120 from rotating in the circumferential direction, and allows the rod 120 to move in the direction of the central axis O. Further, the axial movement protrusion portion 120*e* protrudes from the outer circumferential surface of the rod body 120*a*. Further, the axial movement protrusion portion 12*e* extends from the distal end toward the proximal end side, of the rod body 120*a*, and extends to the position of the distal end side relative to the second branch portion 120*d*. In other words, the axial movement protrusion portion 120*e* extends continuously to the distal end of the rod body 120*a* with a predetermined distance from the second branch portion 120*d* on the distal end side. When the rod 120 is inserted into the cover portion 111, the axial movement protrusion portion 120*e* fits into the axial movement groove portion 111*c* as shown in FIG. 4. In the present embodiment, the axial movement protrusion portion 120*e* includes a pair of axial movement protrusion portions provided in a Y direction.

The fall-off proof portion 120*f* functions to prevent the rod 120 inserted into the barrel body 110 from falling off the barrel body 110. The fall-off proof portion 120*f* is formed to protrude from the outer circumferential surface of the rod body 120*a*. The fall-off proof portion 120*f* has a smaller protrusion width than the second branch portion 120*d*. Specifically, the fall-off proof portion 120*f* protrudes in a tapered shape in which the protrusion width increases from the distal end side to the proximal end side. Further, a surface of the fall-off proof portion 120*f* on the proximal end side is a surface orthogonal to the central axis O. Because of this, the plunger 12 is easily inserted into the barrel 11. Further, the fall-off proof portion 120*f* is provided on the distal end side of the rod body 120*a* relative to the second branch portion 120*d*. Specifically, the fall-off proof portion 120*f* is disposed between the distal end and the proximal end of the axial movement protrusion portion 120*e*. Because of this, as shown in FIG. 3, when the rod body 120*a* is inserted into the cover portion 111 such that the axial movement protrusion portion 120*e* functioning as the rotation restriction portion W fits along the axial movement groove portion 111*c* of the cover portion 111, the fall-off proof portion 120*f* is inserted into the barrel 11 while riding over the insertion through-hole 111*e* formed in the cover portion 111 as shown in FIG. 5. When a force is applied to pull out the rod 120 from the barrel 11, the surface of the fall-off proof portion 120*f* on the proximal end side and the bottom surface of the cover portion 111 abut on each other to prevent the rod 120 from falling off. Further, when a cap K to be described below is removed from the housing 2, the barrel 11 also advances toward the distal end side due to close contact between a needle cap K2 and the barrel 11. However, the fall-off proof portion 120*f* and the cover portion 111 abut on each other to prevent the barrel 11 from advancing. In the present embodiment, the fall-off proof portion 120*f* includes a pair of fall-off proof portions provided in the X direction as shown in FIG. 5.

The distal end protrusion portion 120*h* engages the rod 120 with the piston 121. The distal end protrusion portion 120*h* protrudes from the distal end of the rod body 120*a* toward the distal end side in the direction of the central axis O. Further, the distal end protrusion portion 120*h* is formed smaller than the rod body 120*a* so as to be capable of being inserted into the coupling hole 121*a* of the piston 121. When the rod 120 is inserted into the barrel body 110, the distal end protrusion portion 120*h* is inserted into the coupling hole 121*a* of the piston 121 as shown in FIG. 5.

Figure 6:
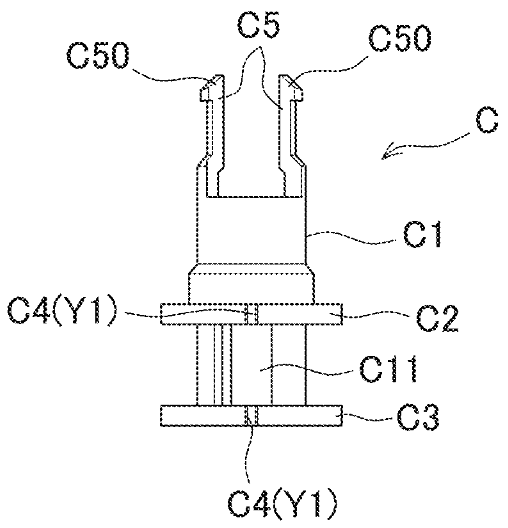
FIG. 6 is a front view of an engaging member of the embodiment.
Figure 6:

As shown in FIG. 1, the engaging member C is disposed in the plunger accommodating portion 20, and is engaged with the plunger 12. As shown in FIG. 6, the engaging member C includes an engaging body C1 that is formed in a tubular shape, a trigger locking portion C5 that is locked to the trigger portion 23 provided in the housing 2, an urging receiving portion C2 that receives urging from the plunger urging portion A, and an urging engaging portion C3 that is formed on one side (distal end side) in the direction of the central axis O relative to the urging receiving portion C2. The engaging body C1 is formed in a tubular shape such that the rod 120 is inserted when the engagement between the plunger 12 and the engaging member C is released. The engaging body C1 is formed in a tubular shape to be larger than the rod 120. Further, the engaging body C1 is provided with an opening passage C11 that penetrates the engaging member C in the radial direction. The opening passage C11 is provided between the urging receiving portion C2 and the urging engaging portion C3 as shown in FIG. 6. Specifically, the opening passage C11 is provided to cut out between the urging receiving portion C2 and the urging engaging portion C3.

The trigger locking portion C5 protrudes from the other side (proximal end side) in the direction of the central axis O of the engaging body C1. The trigger locking portion C5 of the present embodiment is formed in a bifurcated shape as shown in FIG. 6. At each of protruding distal ends of the trigger locking portions C5, a rib C50 is formed in a tapered shape that gradually increases outward as it advances from the protruding distal end toward a protruding proximal end.

The urging receiving portion C2 is formed to protrude from the outer circumferential surface of the engaging body C1. In FIG. 1, the urging receiving portion C2 abuts on the other end of the plunger urging portion A. Because of this, the engaging member C approaches the urging stand portion 200 on the proximal end side of the central axis O, thereby compressing the plunger urging portion A. Further, the urging receiving portion C2 of the present embodiment is formed in an outer flange shape (a round outer flange shape in the present embodiment) protruding in the radially outer direction from the engaging body C1. The urging receiving portion C2 is formed to have substantially the same size as the inner diameter of the plunger accommodating portion 20 having a tubular shape in the radial direction.

The engaging member C is formed with the urging engaging portion C3 that engages with the plunger 12 at the distal end in the direction of the central axis O relative to the urging receiving portion C2. The urging engaging portion C3 has an outer flange shape that protrudes in the radial direction from the outer circumferential surface of the engaging body C1. In the present embodiment, the urging engaging portion C3 has the round outer flange shape.

Figure 7:
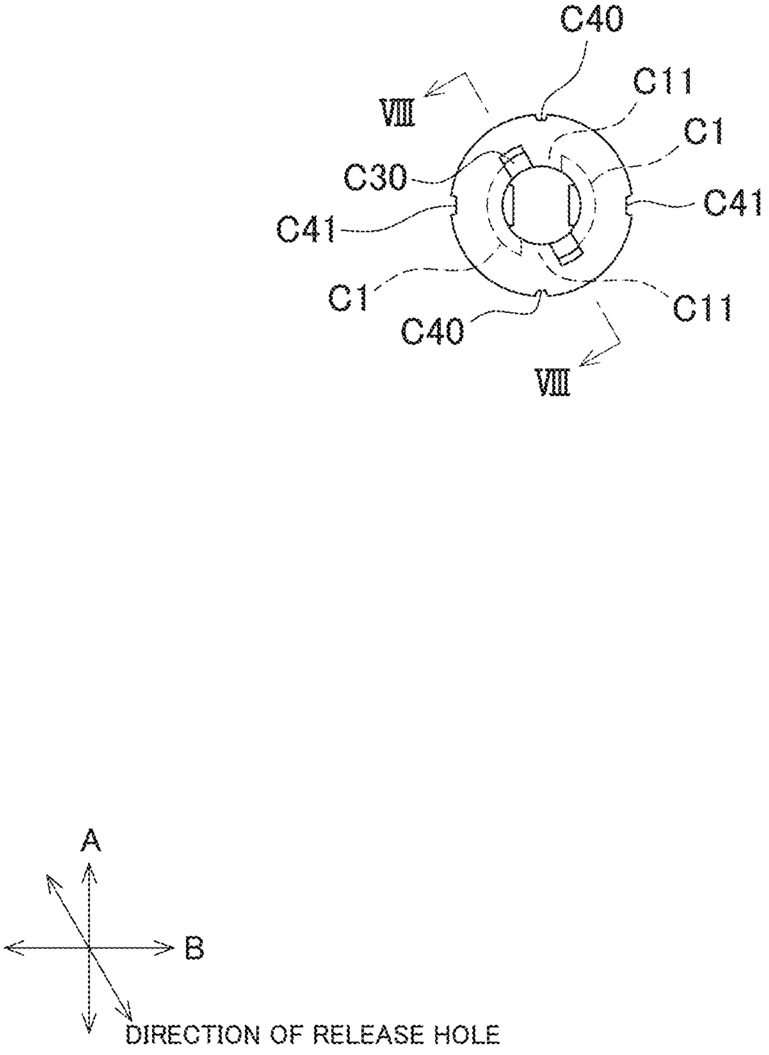
FIG. 7 is a bottom view of the engaging member.
Figure 8:
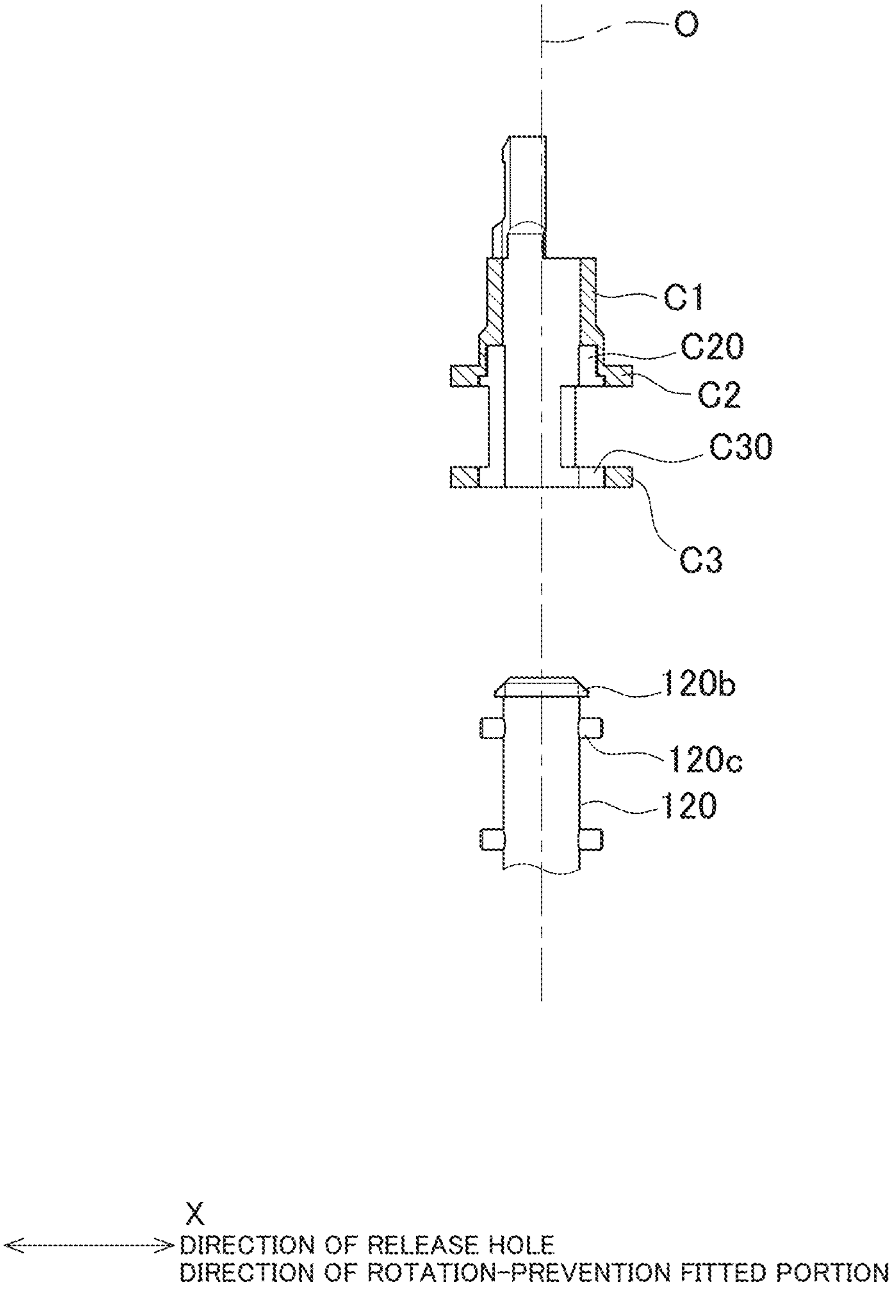
FIG. 8 is a cross-sectional view of the engaging member taken along a line VIII-VIII.

The engaging member C is provided with the release hole C30 and the rotation-prevention fitted portion C20 that is fitted with the rotation-prevention fitting portion 120*b*. The release hole C30 is formed to penetrate the urging engaging portion C3 in the direction of the central axis O as shown in FIG. 8. Further, the release hole C30 is formed to be continuous with the opening passage C11 in the circumferential direction as shown in FIG. 7. The release hole C30 is formed to be larger than the pin portion 120*b* and the first branch portion 120*c*. Because of this, the pin portion 120*b* can pass through the release hole C30, and the proximal end of the rod 120 can be inserted into the engaging member C. Further, the release hole C30 of the present embodiment includes two release holes formed to face each other in the radial direction as shown in FIG. 7. The release hole C30 is formed in a direction different from that of the holding recess portion C4 to be described below in the radial direction. Specifically, the release hole C30 is formed in a direction different from that of the first holding recess portion C40.

The rotation-prevention fitted portion C20 is provided inside the urging receiving portion C2 of the engaging member C. Specifically, the rotation-prevention fitted portion C20 is provided on the proximal end side in the direction of the central axis O from the urging receiving portion C2 as shown in FIG. 8. Further, the rotation-prevention fitted portion C20 of the present embodiment is formed as a pin hole portion C20 into which the pin portion 120*b* provided at the proximal end of the rod 120 is inserted. The pin hole portion C20 of the present embodiment includes two pin hole portions provided in the engaging member C. The rotation-prevention fitted portion C20 is located on the proximal end side in the direction of the central axis O relative to the release hole C30, but has the position in the radial direction that coincides with that of the release hole C30 as shown in FIG. 8. In other words, the rotation-prevention fitted portion C20 and the release hole C30 communicate with each other in the direction of the central axis O.

The engaging member C is formed with the engaging and holding mechanism Y1 that holds the engaging member C so as not to rotate with respect to the plunger accommodating portion 20. Specifically, as shown in FIG. 6, the engaging member C is provided with the holding recess portions C4, which function as the engaging and holding mechanism Y1, in the urging receiving portion C2 and the urging engaging portion C3. The holding recess portion C4 is fitted to the holding projection portion 201 of the plunger accommodating portion 20 in a recess/projection way when the engaging member C is inserted into the plunger accommodating portion 20. In the present embodiment, the holding recess portion C4 includes four holding recess portions provided at intervals of 90° in the engaging member C having substantially a cylindrical shape as shown in FIG. 7. The holding recess portion C4 includes a pair of first holding recess portions C40 formed to face each other in an A direction and a pair of second holding recess portions C41 formed to face each other in a B direction as shown in FIG. 7. In the present embodiment, the first holding recess portion C40 has a smaller width in the circumferential direction than of the second holding recess portion C41. Specifically, the pair of first holding recess portions C40 are fitted to the pair of first holding projection portion 201*a* in a recess/projection way. Further, the pair of second holding recess portions C41 are fitted to the pair of second holding projection portions in a recess/projection way. Thus, when the engaging member C is inserted into the plunger accommodating portion 20, the engaging member C and the plunger accommodating portion 20 can be aligned with each other in the circumferential direction.

Figure 9:
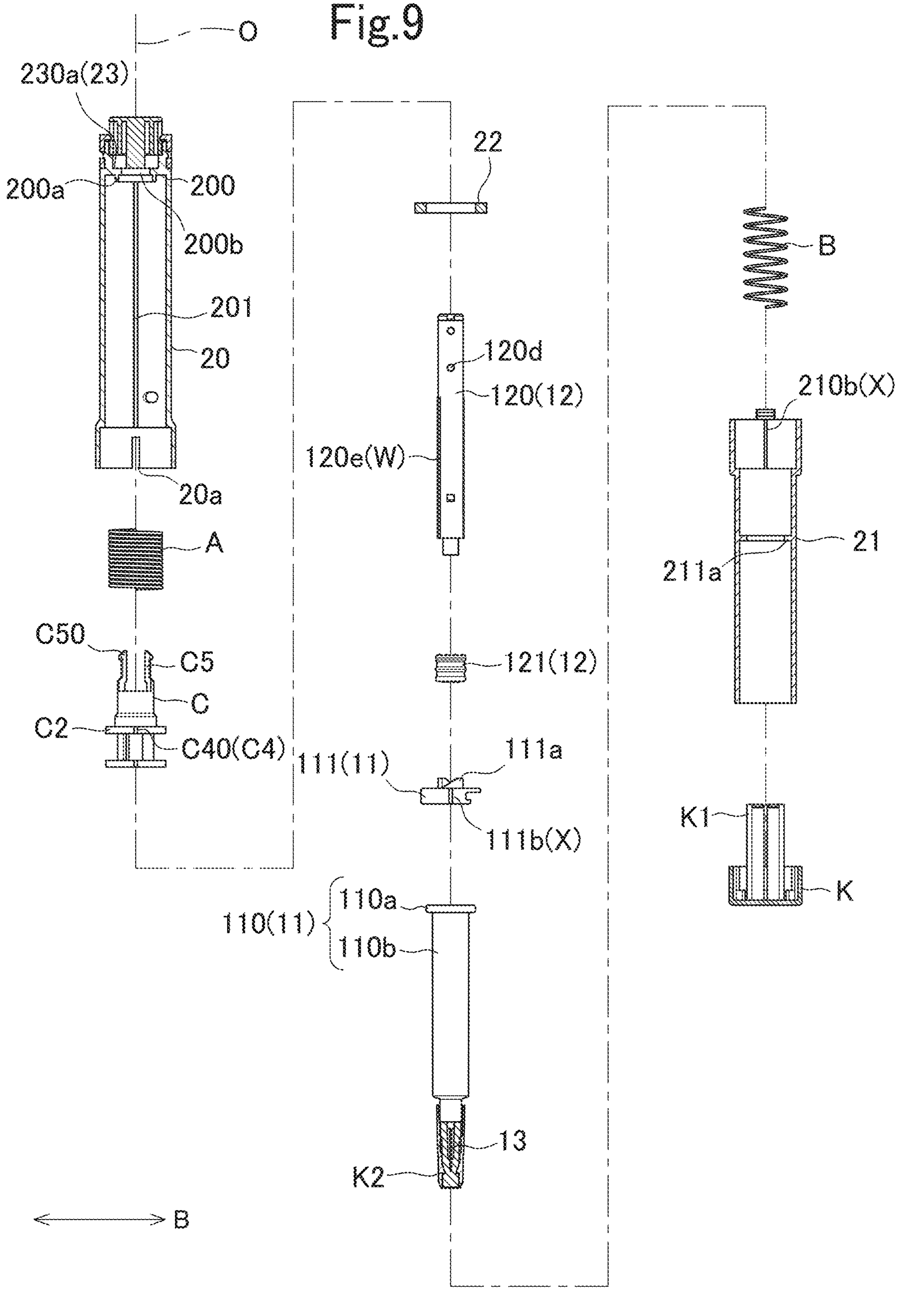
FIG. 9 is a front view showing an exploded state of the injection device of the embodiment, in which a housing and a cap are shown in a cross section.
Figure 10:
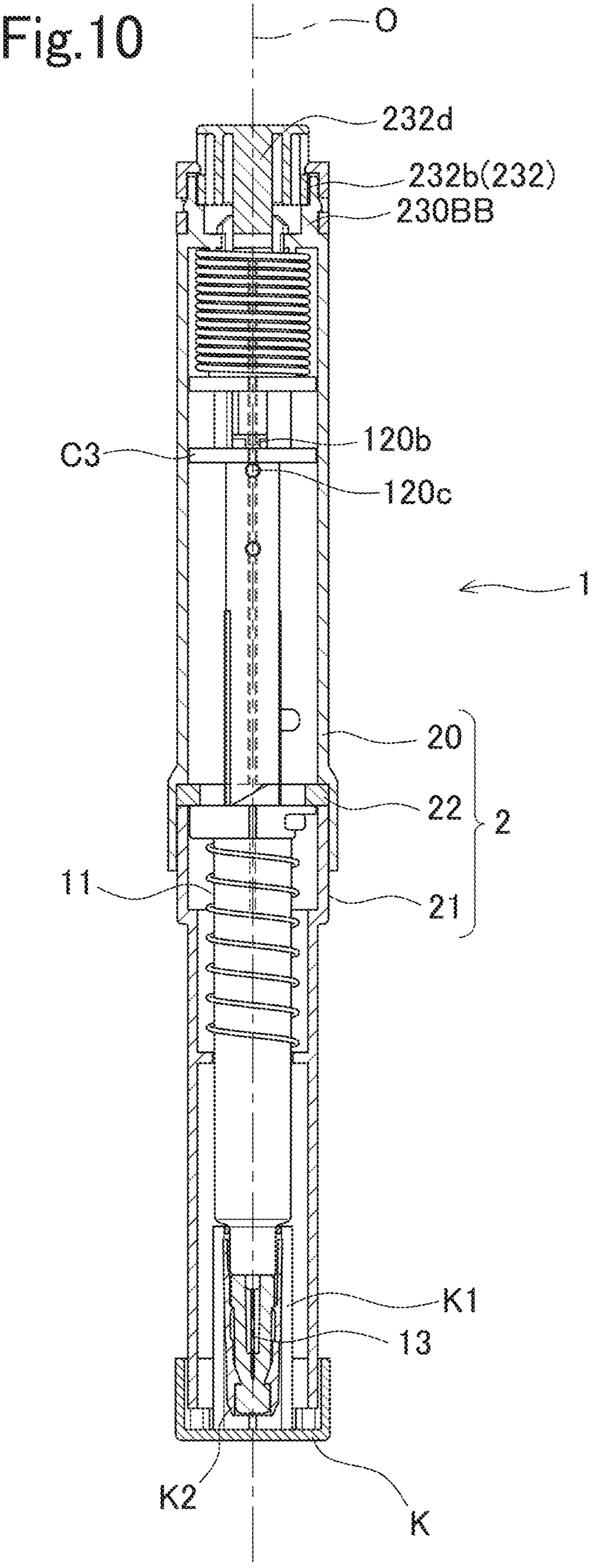
FIG. 10 is a front view showing a housing and a cap in a cross section in an initial state of the injection device of the embodiment.
Figure 11:
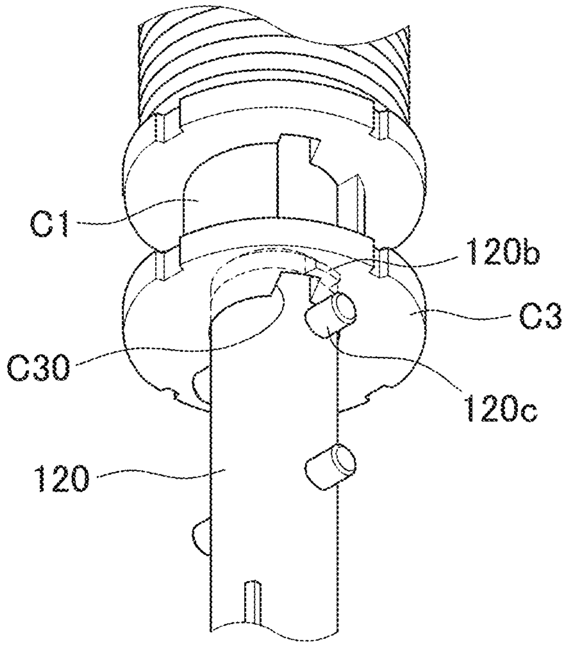
FIG. 11 is a view showing an engagement releasing mechanism in the injection device in the initial state.
Figure 11:
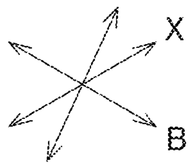

When the injection device 1 of the present embodiment in an initial state is assembled, first, as shown in FIG. 9, the plunger accommodating portion 20, the plunger urging portion A, the engaging member C, the partition portion 22, the rod 120, the syringe 10, the barrel urging portion B, the barrel accommodating portion 21, and the cap K are disposed in the direction of the central axis O. Specifically, for the syringe 10, after the needle cap K2 is attached to the distal end of the barrel 11 to cover the injection needle 13, the piston 121 is inserted into the barrel body 110 filled with the drug solution to be located at the start point, and a prefilled syringe with the cover portion 111 attached to the barrel body 110 is used. The cap K is configured to cover the distal end of the barrel accommodating portion 21 and protects the injection needle 13 accommodated in the barrel accommodating portion 21. Then, after the plunger urging portion A is accommodated in the plunger accommodating portion 20 in the direction of the central axis O, the engaging member C is inserted into the plunger accommodating portion 20. Here, the holding recess portion C4 of the engaging member C is inserted so as to fit into the holding projection portion 201 in the plunger accommodating portion 20. At this time, the trigger lock operation portion 231 and the trigger body portion 232 are rotated around the central axis O with respect to the trigger attaching portion 230. Thus, the lock mechanism portion V is unlocked. In the present embodiment, as shown in FIG. 9, the first holding recess portion C40 is disposed to face the front side, and the engaging member C is advanced into the plunger accommodating portion 20. The engaging and holding mechanism Y1 is formed by the fitting between the holding recess portion C4 and the holding projection portion 201 to hold the engaging member C so as not to rotate around the central axis O with respect to the plunger accommodating portion 20. Further, when the engaging member C is advanced into the plunger accommodating portion 20, the other end side of the plunger urging portion A with one end engaged with the urging stand portion 200 is advanced to the proximal end side of the plunger accommodating portion 20 while resisting the urging of the plunger urging portion A by the urging receiving portion C2 of the engaging member C. Thereafter, the trigger locking portion C5 is inserted into the insertion through-hole 200*b* defined by the urging stand portion 200. Then, the rib C50 of the trigger locking portion C5 is hooked on the hooking portion 230*a*, and the engaging member C is fixed to the trigger portion 23. Thus, the urging of the compressed plunger urging portion A is held so as not to be released. Therefore, the trigger portion 23 is at an urging holding position. Thereafter, the trigger lock operation portion 231 and the trigger body portion 232 are rotated, and the operation of the trigger portion 23 is locked by the lock mechanism portion V. Thereafter, the rod 120 is engaged with the engaging member C accommodated in the plunger accommodating portion 20. Specifically, as shown in FIG. 8, the direction of the release hole C30 provided in the urging engaging portion C3 is made to coincide with the direction (specifically, the X direction) in which the pin portion 120*b* is formed. The rod 120 is inserted into the engaging body C1 such that the pin portion 120*b* is inserted through the release hole C30. Thereafter, the rod 120 or the engaging body C1 is rotated around the central axis O such that the direction of the release hole C30 is different from the X direction as shown in FIG. 11. Further, the urging engaging portion C3 is disposed between the pin portion 120*b* and the first branch portion 120*c*. Thus, as shown in FIGS. 1 and 10, the rod 120 and the engaging member C are engaged with each other. In such an engaged state, the engaging member C and the rod 120 are engaged with each other so as to move in the direction of the central axis O in conjunction with each other. Further, the engaging member C and the rod 120 are in a state of being relatively rotatable around the central axis O.

Subsequently, the barrel urging portion B is housed in the barrel accommodating portion 21 such that the other end of the barrel urging portion B abuts on the urging stand portion 211*a*. Thereafter, the syringe 10 is inserted into the barrel accommodating portion 21. When the syringe 10 is inserted into the barrel accommodating portion 21, the holding recess portion 111*b* of the cover portion 111 attached to the barrel body 110 of the syringe 10 fits into the holding projection portion 210*b* of the barrel accommodating portion 21. The rotation holding mechanism X is formed by the fitting between the holding recess portion 111*b* and the holding projection portion 210*b* to hold the rotary engaged portion (inclined portion) 111*a* of the cover portion 111 so as not to rotate around the central axis O with respect to the barrel accommodating portion 21. Further, after the partition portion 22 is attached to the proximal end of the barrel accommodating portion 21, a pair of outer circumferential surface protrusion portions (not shown), which are provided to extend in the direction of the central axis O on the outer circumferential surface of the barrel accommodating portion 21 on the proximal end side and face each other in the radial direction of the barrel accommodating portion 21, are fitted into a pair of axial cut-out portions 20*a* which extend from the distal end to the proximal end side of the plunger accommodating portion 20, penetrate the circumferential surface of the plunger accommodating portion 20, and face each other in the radial direction of the plunger accommodating portion 20. Thus, the large cylinder-side barrel accommodating portion 210 is inserted into the plunger accommodating portion 20, and thus the barrel accommodating portion 21 and the plunger accommodating portion 20 are engaged with each other. In this state, the barrel 11 abuts on the partition portion 22 by the urging of the barrel urging portion B. The injection needle 13 on the distal end side is accommodated in the barrel accommodating portion 21, and the barrel 11 is at a first position. Here, the rod 120 accommodated in the plunger accommodating portion 20 is inserted into the barrel 11 when the barrel accommodating portion 21 and the plunger accommodating portion 20 are engaged with each other. In the present embodiment, the axial movement protrusion portion 120*e* and the axial movement groove portion 111*c* are fitted to form the rotation restriction portion W that restricts the plunger 12 from rotating around the central axis O with respect to the barrel 11. Further, the second branch portion 120*d* as the rotary engaging portion 120*d* of the plunger 12 and the rotary engaged portion 111*a* of the barrel 11 are aligned with each other in the direction of the central axis O. Specifically, as shown in FIG. 4, the second branch portion 120*d* and the rotary engaged portion 111*a* are disposed so as to overlap each other in the X direction. Therefore, when the plunger 12 is pushed toward the distal end of the barrel 11 from the position close to the distal end side than the proximal end of the barrel 11, the plunger 12 moves in the direction of the central axis O while being restricted from rotating by the rotation restriction portion W. Then, when the plunger 12 reaches a position immediately before reaching the distal end of the barrel 11, the second branch portion 120*d* of the plunger 12 abuts on the inclined portion 111*a* of the barrel 11. In other words, the rotation restriction portion W determines the engagement position between the second branch portion 120*d* (rotary engaging portion 120*d*) of the plunger 12 and the inclined portion 111*a* (rotary engaged portion 111*a*) of the barrel 11.

Thereafter, the cap K is attached to the distal end side of the housing 2. The cap K closes the distal end of the housing 2, and protects the injection needle 13 in the housing 2 from external factors. The cap K of the present embodiment is formed to be larger than the housing 2 and is formed in a cylindrical shape such that the housing 2 can be inserted thereinto. Further, the cap K includes a needle cap holding portion K1 that is inserted into the housing 2 and covers externally the injection needle 13. The needle cap holding portion K1 fits the needle cap K2 attached to the barrel 11 to cover externally the injection needle 13. In this way, the syringe 10 is inserted into the housing 2 to assemble the injection device 1 in the initial state as shown in FIG. 10.

Subsequently, a method of using the injection device 1 of the present embodiment will be described. FIG. 10 shows an initial state of the injection device 1 of the present embodiment. In such a state, the cap K is attached to the distal end of the housing 2. Because of this, when the injection device 1 of the present embodiment is used, first, the cap K is removed from the housing 2. Thus, as shown in FIG. 1, an opening is formed at the distal end of the housing 2. At this time, the needle cap K2 at the distal end of the barrel 11 is removed together with the cap K in a state of being fitted to the needle cap holding portion K1.

Subsequently, as shown in FIG. 12, the injection needle 13 accommodated in the housing 2 is allowed protrude from the opening at the distal end of the housing 2. In the present embodiment, as shown in FIG. 1, in the injection device 1 from which the cap K is removed, the injection needle 13 is accommodated in the housing 2 and the barrel 11 is at the first position. Because of this, the lock of the trigger portion 23 is released, and the trigger portion 23 is pushed toward the plunger accommodating portion 20. Specifically, the trigger lock operation portion 231 and the trigger body portion 232 are rotated around the central axis O with respect to the trigger attaching portion 230. Thus, the release groove 232*ba* of the trigger body portion 232 and the lock step portion 230BB of the trigger attaching portion 230 are aligned to release the lock of the trigger portion 23. Further, the flat plate portion 232*d* is rotated from the state shown in FIG. 10 such that a thickness thereof is aligned with the direction in which the pair of trigger locking portions C5 face each other. Thereafter, the trigger body portion 232 is pushed toward the distal end side in the direction of the central axis O. The inner skirt portion 232*c* as the trigger activation portion abuts on an inclined surface at the distal end of the trigger locking portion C5 of the engaging member C locked to the hooking portion 230*a*. Specifically, the inner skirt portion 232*c* abuts on the rib C50. Thus, the trigger locking portion C5, which is allowed to bend inward by the rotation of the flat plate portion 232*d*, bends in the radially inward direction, and the engagement between the trigger locking portion C5 and the hooking portion 230*a* is released. Therefore, as shown in FIG. 12, the engagement between the trigger portion 23 and the engaging member C is released. Therefore, the urging of the plunger urging portion A held in the compressed state is released. Accordingly, the trigger portion 23 moves from an urging holding position, at which the urging force of the plunger urging portion A is held so as not to be released, to an urging force releasing position at which the urging force of the plunger urging portion A is released.

The urging receiving portion C2 is pushed by the urging of the released plunger urging portion A. Further, the engaging member C and the syringe 10 engaged with the engaging member C advance to the distal end side of the plunger accommodating portion 20. In the present embodiment, the barrel urging portion B is set to have a weaker urging force than the plunger urging portion A. Because of this, the barrel urging portion B is pushed and compressed against the bottom surface of the cover portion 111 as the engaging member C advances toward the distal end side of the plunger accommodating portion 20. Further, the cover portion 111 moves in the direction of the central axis O along the holding projection portion 210*b* in which the holding recess portion 111*b* is provided in the large cylinder-side barrel accommodating portion 210. The cover portion 111 moves until the bottom surface abuts on the barrel receiving portion 210*a*. Because of this, the barrel urging portion B is compressed until the bottom surface of the cover portion 111 abuts on the barrel receiving portion 210*a* as shown in FIG. 12. Further, as the barrel 11 moves toward the distal end side of the barrel accommodating portion 21, the injection needle 13 provided at the distal end of the barrel body 110 protrudes from the barrel accommodating portion 21. Because of this, the barrel 11 located at the first position moves to the second position. When the engaging member C and the syringe 10 move, the engaging member C is restricted from rotating around the central axis O by the engaging and holding mechanism Y1. Further, the rotary engaged portion 111*a* is restricted from rotating around the central axis O by the rotation holding mechanism X. Further, the plunger 12 is restricted from rotating around the central axis O by the rotation restriction portion W. Therefore, it is possible to prevent the engaging member C from being accidentally released from the plunger 12. Further, it is possible to prevent the engagement position of the rotary engaging portion 120*d* and the rotary engaged portion 111*a* from deviating from each other.

Figure 13:
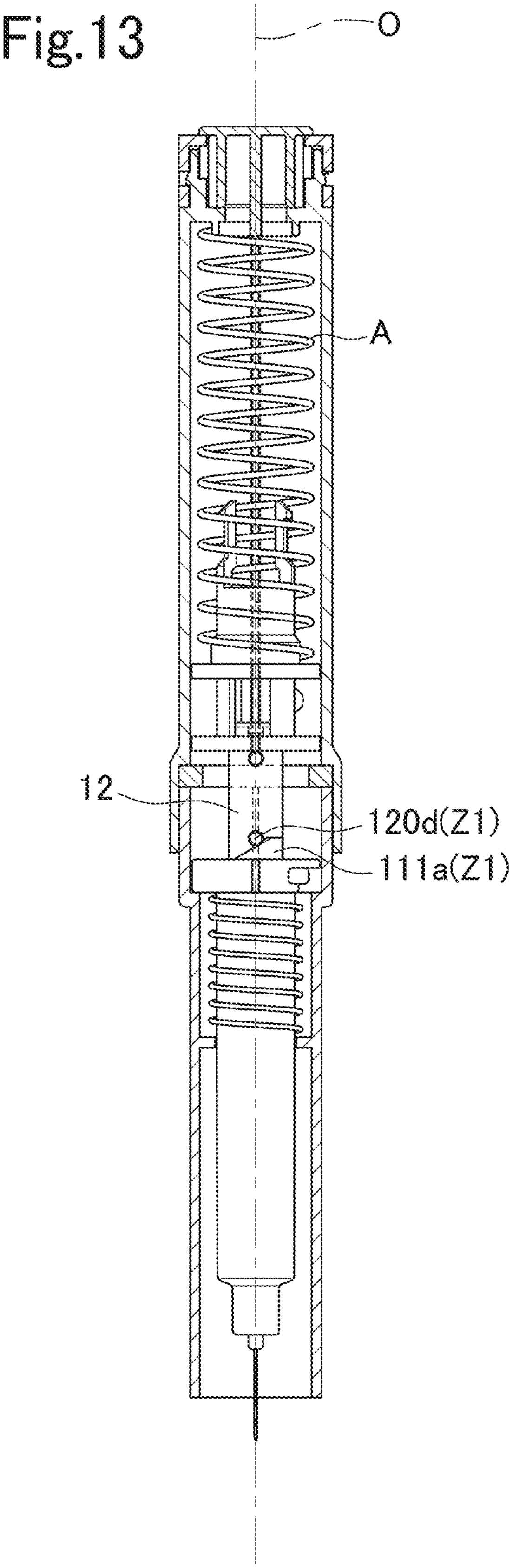
FIG. 13 is a view showing the injection device of the embodiment, in which a housing is shown in a cross section, and a rotary engaging portion and a rotary engaged portion are engaged with each other.

Subsequently, when the cover portion 111 abuts on the barrel receiving portion 210*a*, the movement of the barrel 11 toward the distal end side is restricted. On the other hand, the engaging member C and the plunger 12 further move toward the distal end side in the direction of the central axis O by the urging of the plunger urging portion A. Therefore, the plunger 12 advances in the barrel 11. Here, the engaging member C moves toward the distal end side of the plunger accommodating portion 20 such that the holding recess portion C4 is located along the holding projection portion 201 provided in the plunger accommodating portion 20. When the plunger 12 advances in the barrel 11, the axial movement protrusion portion 120*e* moves along the axial movement groove portion 111*c* provided in the cover portion 111 as shown in FIG. 12. In other words, even when the plunger 12 is pushed into the barrel 11, the engaging member C is restricted from rotating around the central axis O by the engaging and holding mechanism Y1. Further, the rotary engaged portion 111*a* of the barrel 11 is restricted from rotating around the central axis O by the rotation holding mechanism X. Further, the plunger 12 (rotary engaging portion 120*d*) is restricted from rotating around the central axis O by the rotation restriction portion W. Further, when the plunger 12 advances in the barrel 11, the piston 121 engaged with the rod 120 advances in the barrel body 110. Therefore, the piston 121 pushes the drug solution out of the barrel from the injection needle 13. Then, when the plunger 12 approaches the distal end of the barrel 11, the axial movement protrusion portion 120*e* extending from the distal end of the rod body 120*a* up to the distal end side from the second branch portion 120*d* comes out of the axial movement groove portion 111*c* to the distal end side. Because of this, the restriction by the rotation restriction portion W is released. In other words, the plunger 12 (rotary engaging portion 120*d*) comes into a state of being rotatable around the central axis O with respect to the rotary engaged portion 111*a* of the barrel 11. Then, as shown in FIG. 13, the second branch portion 120*d* as the rotary engaging portion abuts on the inclined portion 111*a* as the rotary engaged portion, and the engagement releasing mechanism Z1 operates.

Figure 14:
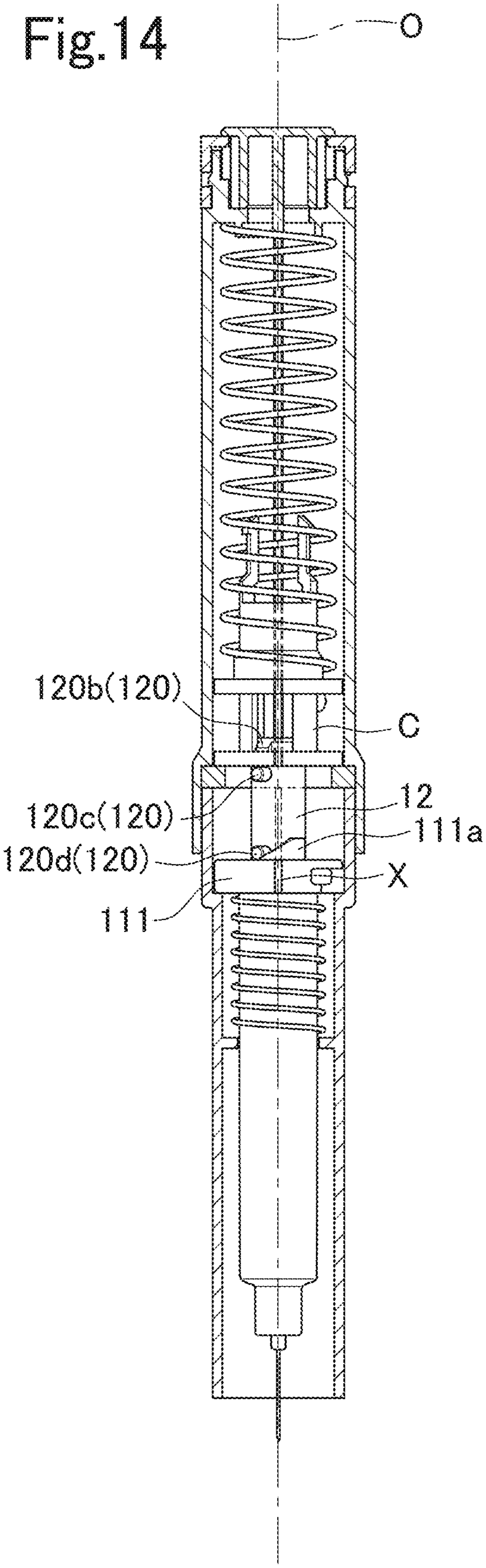
FIG. 14 is a view showing the injection device of the embodiment, in which a housing is shown in a cross section and a plunger rotates around a central axis.

By the force generated toward the distal end side in the direction of the central axis O by the urging of the plunger urging portion A, the plunger 12 moves in the barrel 11 from the position (start point) closer to the distal end side than the proximal end of the barrel 11 to the distal end (end point) of the barrel 11. Then, after the plunger 12 reaches a position immediately before the distal end of the barrel 11, the second branch portion 120*d* slides along the inclined portion 111*a* (specifically, the inclined surface 111*aa*). Because of this, as shown in FIG. 13, the second branch portion 120*d* changes from the state in which the second branch portion 120*d* abuts on the inclined portion 111*a* (specifically, the inclined surface 111*aa*) to the state of sliding along the inclined portion 111*a* as shown in FIG. 14. Here, the engaging member C is restricted from rotating by the engaging and holding mechanism Y1, and the rotary engaged portion 111*a* is restricted from rotating by the rotation holding mechanism X. On the other hand, the restriction of the rotation restriction portion W for restricting the rotation of the plunger 12 is released. Therefore, the plunger 12 and the engaging member C rotate relative to each other around the central axis O. Specifically, in the present embodiment, the plunger 12 rotates around the central axis O with respect to the engaging member C. Further, the rotary engaging portion 120*d* of the plunger 12 rotates around the central axis O with respect to the rotary engaged portion 111*a*. Specifically, the rotary engaging portion 120*d* rotates about 30° to the left in a state of being engaged with the inclined surface 111*aa* of the inclined portion 111*a* as shown in FIG. 13. Therefore, the rotary engaging portion 120*d* moves toward the upper surface of the cover portion 111 as shown in FIG. 14.

Figure 15:
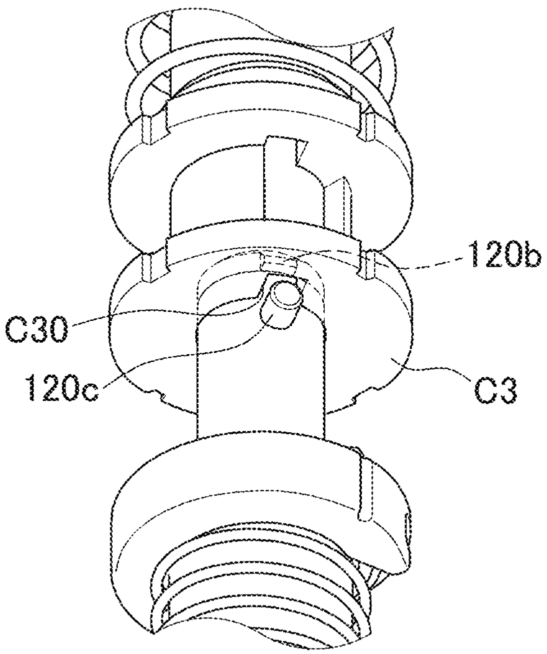
FIG. 15 is a view showing the engagement releasing mechanism in a state where the plunger rotates around the central axis.
Figure 15:
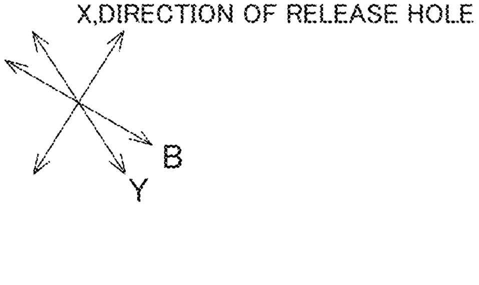

Further, as shown in FIG. 14, the pin portion 120*b* and the first branch portion 120*c* rotate by the rotation of the plunger 12. Here, the pin portion 120*b* and the first branch portion 120*c* are disposed in the X direction in the rod 120 of the present embodiment. Because of this, as shown in FIG. 15, when the first branch portion 120*c* is disposed at the position coinciding with that of the release hole C30 in the circumferential direction by the rotation of the plunger 12, the pin portion 120*b* is also disposed at the position coinciding with that of the release hole C30 in the circumferential direction. Therefore, the engagement releasing mechanism Z1 operates, and thus the engagement between the urging engaging portion C3 and the urging engaged portion 120*c* is released. Thus, the engagement between the plunger 12 and the engaging member C is released. At this time, the plunger 12 has reached the end point.

Figure 16:
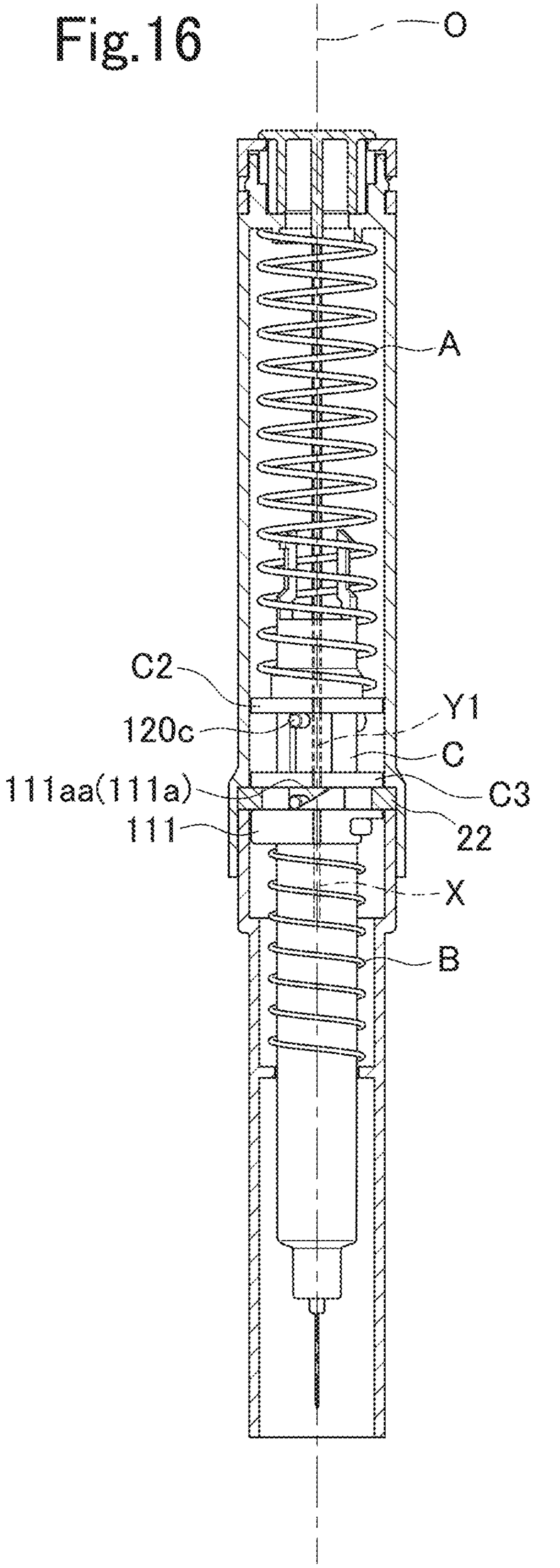
FIG. 16 is a view showing the injection device of the embodiment, in which a housing is shown in a cross section and an injection needle is returned to the inside of the housing.
Figure 17:
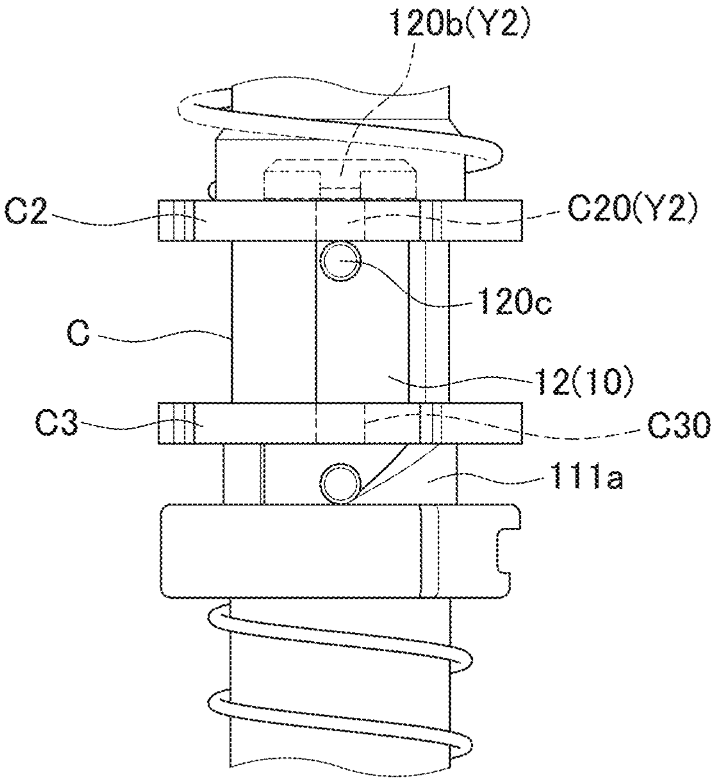
FIG. 17 is a view showing a state where a rotation-prevention fitting portion and a rotation-prevention fitted portion are fitted in a state where the injection needle is returned to the inside of the housing.

When the engagement between the urging engaging portion C3 and the urging engaged portion 120*c* is released, the urging against the syringe 10 of the plunger urging portion A is released. Because of this, the plunger urging portion A pushes only the engaging member C toward the distal end side. On the other hand, the barrel urging portion B compressed by the plunger urging portion A is released. Because of this, the barrel urging portion B pushes the syringe 10 toward the proximal end side. Therefore, as shown in FIG. 16, the engaging member C moves to a position where the urging engaging portion C3 closely faces the partition portion 22 in a state of being restricted from rotating by the engaging and holding mechanism Y1, and is urged and fixed at this position. Further, the barrel 11 (specifically, the cover portion 111) moves to a position at which it closely faces the partition portion 22 in a state where the rotary engaged portion 111*a* is restricted from rotating by the rotation holding mechanism X. The barrel 11 is urged and fixed at this position. Here, one end side of the barrel urging portion B abuts on the bottom surface of the cover portion 111. Because of this, the cover portion 111 is pushed toward the partition portion 22 by the urging of the barrel urging portion B. Then, in the present embodiment, when the barrel 11 abuts on the bottom surface of the partition portion 22 as shown in FIG. 16, the inclined portion 111*a* enters the through hole 220 of the partition portion 22. Further, when the cover portion 111 is pushed toward the partition portion 22, the plunger 12 moves to the proximal end side of the housing 2 together with the barrel 11. Therefore, the first branch portion 120*c* is inserted through the release hole C30 of the engaging member C, and the pin portion 120*b* is fitted into the rotation-prevention fitted portion C20 as shown in FIG. 17. Therefore, by the engagement between the rotation-prevention fitting portion (pin portion) 120*b* and the rotation-prevention fitted portion C20, the plunger 12 is prevented from rotating in a reverse direction. Thus, the plunger 12 functions as a reverse rotation prevention mechanism Y2 that prevents the plunger 12 from rotating in a direction (reverse rotation) opposite to the rotation generated during the releasing of the engagement with the engaging member C. In this way, when the engagement releasing mechanism Z1 operates, the engaging member C closely faces the partition portion 22 while being restricted from rotating, and is urged and fixed. Further, a reverse rotation prevention mechanism Y2 is formed with respect to the engaging member C such that the plunger 12 does not rotate in the reverse direction. Therefore, a reverse rotation prevention means Y is formed such that the disengaged plunger 12 is held so as not to rotate in the reverse direction. The rotary engaged portion 111*a* (the cover portion 111) of the barrel 11 closely faces the partition portion 22 while being restricted from rotating, and is urged and fixed. In this way, the rotation of the engaging member C, the plunger 12, and the rotary engaged portion 111*a* after the release of engagement is restricted, and thus the engaging member C and the plunger 12 are held in the state of being disengaged from each other. Therefore, as shown in FIG. 16, the urging engaged portion (the first branch portion) 120*c* is located between the urging engaging portion C3 closely facing the partition portion 22 and the urging receiving portion C2. In this way, after the engagement is released, the syringe 10 is urged and fixed at a position closer to the proximal end side than the urging engaging portion C3 of the engaging member C by the barrel urging portion B urging the syringe 10 toward the proximal end side. Further, the urging engaging portion C3 of the engaging member C is urged and fixed at a position closer to the distal end side than the urging engaged portion 120*c* by the urging of the plunger urging portion A toward the distal end side. In this way, the engaging member C and the plunger 12 are held in the state of being disengaged from each other.

In the present embodiment, the plunger 12 moves to the proximal end side of the housing 2, the first branch portion 120*c* is inserted through the release hole C30 of the engaging member C, and the pin portion 120*b* is fitted into the rotation-prevention fitted portion C20. At this time, in the direction of the central axis O and the circumferential direction, the first branch portion 120*c* is disposed at the same position as the through hole 202 provided in the circumferential direction of the plunger accommodating portion 20. Because of this, the first branch portion 120*c*, which is visible in the housing 2 from the outside of the housing 2 through the through hole 202, functions as an indicator indicating that a drug administration is completed. In this case, it is preferable that the first branch portion 120*c* has a color different from that of other members, for example, the rod body 120*a*. Thus, it is possible to more reliably indicate that the drug administration is completed.

The method of using the injection device 1 of the present embodiment has been described above. The injection device 1 of the present embodiment includes: the syringe 10 including the barrel 11 provided with the injection needle 13 at the distal end thereof and the plunger 12 inserted into the barrel 11 so as to be capable of reciprocating between the proximal end side of the barrel 11 as a start point and the distal end side as an end point; the housing 2 formed in a tubular shape to accommodate the syringe 10, the housing 2 including the barrel accommodating portion 21 formed on one side in the direction of the central axis O and accommodating the barrel 11 to be movable between the first position in a state where the injection needle 13 is accommodated in the housing and the second position in a state where the injection needle 13 protrudes from one side of the housing 2 at a predetermined distance from the first position to one side and the plunger accommodating portion 20 formed on the other side relative to the barrel accommodating portion 21 and accommodating the plunger 12 protruding from the proximal end side of the barrel 11; the barrel urging portion B provided in the barrel accommodating portion 21 and urging the barrel 11 from the one side of the housing 2 to the other side on which the injection needle 13 is accommodated in the housing 2; the engaging member C disposed in the plunger accommodating portion 20 and engaged with the plunger 12; the plunger urging portion A engaged with the engaging member C and urging the plunger 12 from the start point toward the end point; the trigger portion 23 configured to include the urging force holding position at which the trigger portion 23 holds the urging force of the plunger urging portion A so as not to release the urging force in a state where the barrel 11 accommodates the injection needle 13 by the barrel urging portion B and the state where the plunger 12 resists against the urging force of the plunger urging portion A and the distal end of the plunger is located at the position of the start point, and to move from the urging force holding position to the urging force releasing position at which the urging force is released by a predetermined operation by a user, and an engagement releasing mechanism Z1 configured to release the engagement between the plunger 12 and the engaging member C and to cause the plunger 12 to be located at the end point in a manner that as the trigger portion 23 moves to the urging force releasing position, the plunger 12 moves from the start point toward the end point by the urging force of the plunger urging portion A and the plunger 12 and the engaging member C rotate relative to each other around the central axis O.

In the injection device 1 having the above configuration, when a predetermined operation is performed on the trigger portion 23, the urging of the plunger urging portion A is released, and thus the syringe 10 moves to one side in the direction of the central axis O by the urging of the plunger urging portion A until the injection needle 13 protrudes from the housing 2. When the syringe 10 moves until the injection needle 13 protrudes from the housing 2, the barrel 11 is held in position against the urging of the plunger urging portion A by the urging force of the barrel urging portion B, whereas the plunger 12 subsequently moves to one side in the direction of the central axis O by the urging of the plunger urging portion A and is pushed against the barrel 11, and the drug solution in the barrel 11 is discharged. Then, when the plunger 12 moves to the end point, the discharging is completed. In the injection device 1 of the present embodiment, since the engagement releasing mechanism Z1 is configured to release the engagement between the plunger 12, which has moved toward the end point, and the engaging member C by a relative rotation, the urging of the plunger urging portion A toward the plunger 12 is released when the engagement between the plunger 12 and the engaging member C is released. Accordingly, the syringe 10 is urged to the other side in the direction of the central axis O by the urging of the barrel urging portion B, whereby the injection needle 13 is pulled into the housing 2.

Specifically, according to the injection device 1 of the present embodiment, the engagement releasing mechanism Z1 is configured to release the engagement between the plunger 12, which has moved toward the end point from the start point, and the engaging member C by causing the plunger 12 and the engaging member C to rotate relative to each other. Because of this, the engagement between the plunger 12 and the engaging member C is released at the end point of the movement of the plunger 12, and thus the urging of the plunger urging portion A toward the plunger 12 is released. The syringe 10 is pushed to the other side in the direction of the central axis O by the urging of the barrel urging portion B. Thus, the injection needle 13 can be pulled into the housing 2.

In the injection device of the present embodiment, the engagement releasing mechanism includes the rotary engaging portion provided on the plunger and the rotary engaged portion provided on the barrel, and is configured such that when the plunger moves from the start point toward the end point, the rotary engaging portion and the rotary engaged portion are engaged with each other, and thus the plunger rotates around the central axis to release the engagement between the plunger and the engaging member.

Therefore, according to the injection device 1 having the above configuration, since the engagement position between the rotary engaging portion 120*d* and the rotary engaged portion 111*a* can be set according to the moving position of the plunger 12 with respect to the barrel 11, the engagement can be released according to the end point of the movement of the plunger 12. Specifically, when the plunger 12 moves from the position closer to the distal end side than the proximal end of the barrel 11 to the position immediately before reaching the distal end of the barrel 11, the second branch portion 120*d* engages with the inclined portion 111*a*, and the second branch portion 120*d* slides along the inclined portion 111*a*. Thus, the plunger 12 rotates around the central axis, and as shown in FIG. 15, the pin portion 120*b* and the first branch portion 120*c* are disposed at the position that coincides with the release hole C30 in the circumferential direction, such that the engagement between the plunger 12 and the engaging member C is released. The barrel urging portion B pushes the cover portion 111 toward the partition portion 22. Therefore, as show in FIG. 16, the plunger 12 is accommodated in the engaging member C, and the barrel 11 moves toward the partition portion 22. Therefore, the injection needle 13 can be pulled inside the housing 2.

Further, according to the injection device 1 of the present embodiment, the plunger 12 is inserted into the engaging member C. Because of this, after the engagement between the plunger 12 and the engaging member C is released, the urging engaged portion 120*c* is urged and fixed between the urging engaging portion C3 closely facing the partition portion 22 and the urging receiving portion C2. Therefore, since the urging engaging portion C3 and the urging engaged portion 120*c* can be prevented from returning to the engaged state, it is possible to prevent the injection needle 13 once accommodated from accidentally protruding again.

Further, according to the injection device 1 of the present embodiment, the engagement releasing mechanism Z1 includes the rotary engaging portion 120*d* provided on the plunger 12 and the rotary engaged portion 111*a* provided on the barrel 11, and is configured such that the rotary engaged portion 111*a* engages with the rotary engaging portion 120*d* when the plunger 12 moves from the start point to the position immediately before reaching the end point, whereby the plunger 12 rotates around the central axis O and the engagement between the plunger 12 and the engaging member C is released. Because of this, since the engagement position between the rotary engaging portion 120*d* and the rotary engaged portion 111*a* can be set according to the moving position of the plunger 12 with respect to the barrel 11, the engagement can be released immediately before the end point of the movement of the plunger 12.

Further, the injection device 1 of the present embodiment includes the rotation holding mechanism X that holds the rotary engaged portion 111*a* so as not to rotate with respect to the barrel accommodating portion 21. The injection device 1 includes the reverse rotation prevention means Y that holds the plunger 12 disengaged from the engaging member C so as not to rotate in the reverse direction by operating the engagement releasing mechanism Z1. Because of this, the rotary engaging portion 120*d* and the rotary engaged portion 111*a* are engaged with each other to rotate the plunger 12, and the plunger 12 rotates in the reverse direction after the engagement with the engaging member C is released, whereby it is possible to prevent the engagement state from occurring again.

Further, according to the injection device 1 of the present embodiment, the reverse rotation prevention means Y includes the engaging and holding mechanism Y1 that holds the engaging member C so as not to rotate with respect to the plunger accommodating portion 20 and the reverse rotation prevention mechanism Y2 that holds the disengaged plunger 12 so as not to rotate in the reverse direction with respect to the engaging member C. Because of this, by the configuration that the rotary engaged portion 111*a* and the engaging member C are prevented from rotating, and the disengaged plunger 12 is prevented from rotating in the reverse rotation, it is possible to surely prevent the reverse rotation and it is possible to effectively prevent the engagement state from occurring again.

Further, according to the injection device 1 of the present embodiment, the reverse rotation prevention mechanism Y2 includes the rotation-prevention fitting portion 120*b* provided at the other end of the plunger 12 and the rotation-prevention fitted portion C20 provided at the urging receiving portion C2 of the engaging member C, and is configured to prevent the plunger 12 from rotating in the reverse direction in such a way that the engagement between the urging engaging portion C3 and the urging engaged portion 120*c* is released by the engagement releasing mechanism Z1, the engaging member C closely faces the partition portion 22, and the rotation-prevention fitting portion 120*b* and the rotation-prevention fitted portion C20 are fitted to each other in the state where the urging engaged portion 120*c* is located between the urging engaging portion C3 and the urging receiving portion C2. Because of this, the rotary engaged portion 111*a* of the barrel 11 is prevented from rotating by the rotation holding mechanism X, and the engaging member C is prevented from rotating by the engaging and holding mechanism Y1. The urging engaged portion 120*c* of the plunger 12 is located between the urging engaging portion C3 and the urging receiving portion C2 of the engaging member C. Further, the rotation-prevention fitting portion 120*b* and the rotation-prevention fitted portion C20 are fitted to each other to prevent the reverse rotation of the plunger 12. Therefore, it is possible to reliably hold the state where engagement between the plunger and the engaging member C is released and to thereby prevent the injection needle 13 from protruding again.

As described above, according to the present embodiment, since the engagement between the plunger 12 and the engaging member C is released by rotating both the members relative to each other, the injection needle can be reliably returned.

Further, the injection device is not limited to the above embodiment, and it goes without saying that various modifications can be made without departing from the gist of the present invention. For example, other configurations can be added to the configuration of the above embodiment. Further, a part of the configuration of the above embodiment can be replaced with another configuration. Further, a part of the configuration of the above embodiment can be deleted.

Figure 18:
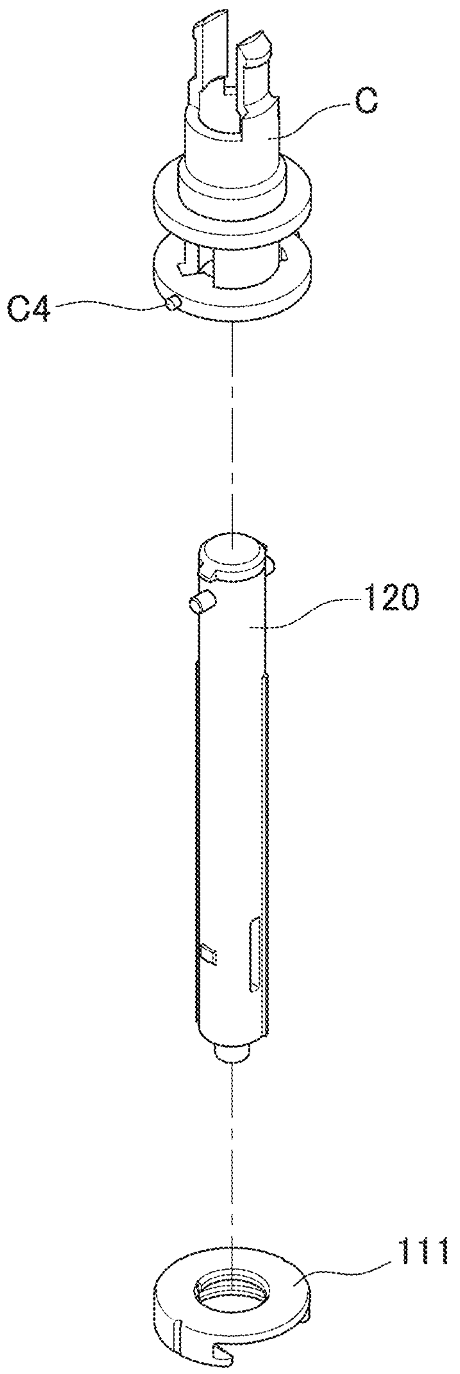
FIG. 18 is a perspective view of an engaging member, a rod, and a cover portion according to a modified example of the injection device.
Figure 19:
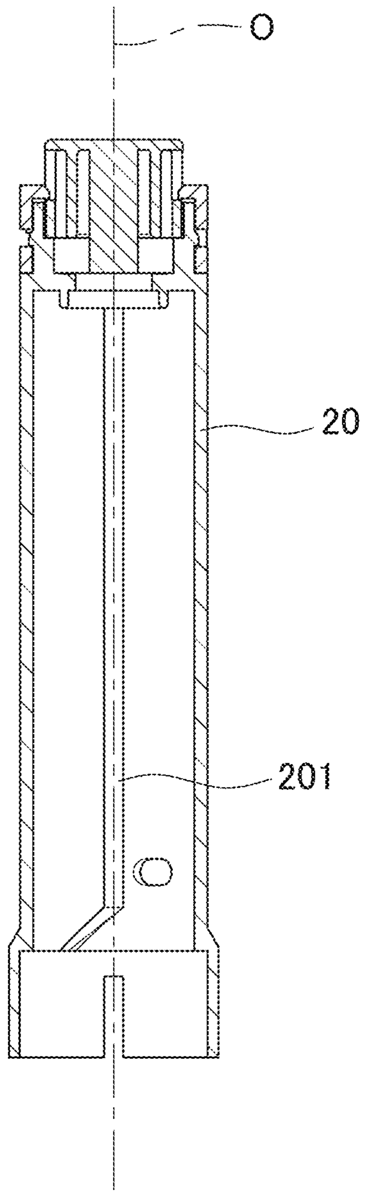
FIG. 19 is a cross-sectional view of a plunger accommodating portion according to the modified example of the injection device.

In the present embodiment, the case has been described in which the engagement releasing mechanism Z1 rotates the plunger 12. However, the present invention includes a case of rotating the engaging member C or a case of rotating both the plunger 12 and the engaging member C in opposite directions without being limited thereto. In the case of rotating the engaging member C, for example, the rotary engaging portion can be provided on the engaging member C, and the rotary engaged portion can be provided on the barrel or the housing. For example, the holding projection portion C4 as the rotary engaging portion can be provided in the urging engaging portion of the engaging member C as shown in FIG. 18, and the holding recess portion 201 as the rotary engaged portion can be provided in the plunger accommodating portion 20 as shown in FIG. 19. In this case, the holding recess portion 201 provided in the plunger accommodating portion 20 is provided so as to rotate the engaging member C. Specifically, the holding recess portion 201 extending in the direction of the central axis O from the proximal end to the distal end side has the distal end side of the central axis O that is inclined in the circumferential direction toward the distal end. Thus, when the holding projection portion C4 of the engaging member C passes through the holding recess portion 201 on the distal end side that is inclined, the engaging member C can be rotated. In this case, for example, the plunger urging portion can be formed by a torsion spring. In other words, when the engagement between the hooking portion and the trigger locking portion is released and the plunger urging portion is urged toward the distal end side of the plunger accommodating portion, the engaging member C is moved to the distal end side of the plunger accommodating portion by the urging. Then, using the rotation around the central axis O of the plunger urging portion formed by the torsion spring, the holding projection portion C4 of the engaging member C is passed through the holding recess portion 201 on the inclined distal end side. In this way, the engaging member C can be rotated. When the plunger urging portion is formed by the torsion spring, the distal end side of the holding recess portion 201 can be a horizontal groove.

Subsequently, referring to FIGS. 20 to 28, an injection device of a second embodiment will be described that is configured to rotate an engaging member using a rotation around a central axis of a plunger urging portion. In the description of the injection device of the second embodiment, the same components as those of the first embodiment are denoted by the same reference numerals, parts similar to those of the first embodiment will not be repeatedly described, and differences from the first embodiment will be described.

Figure 20:
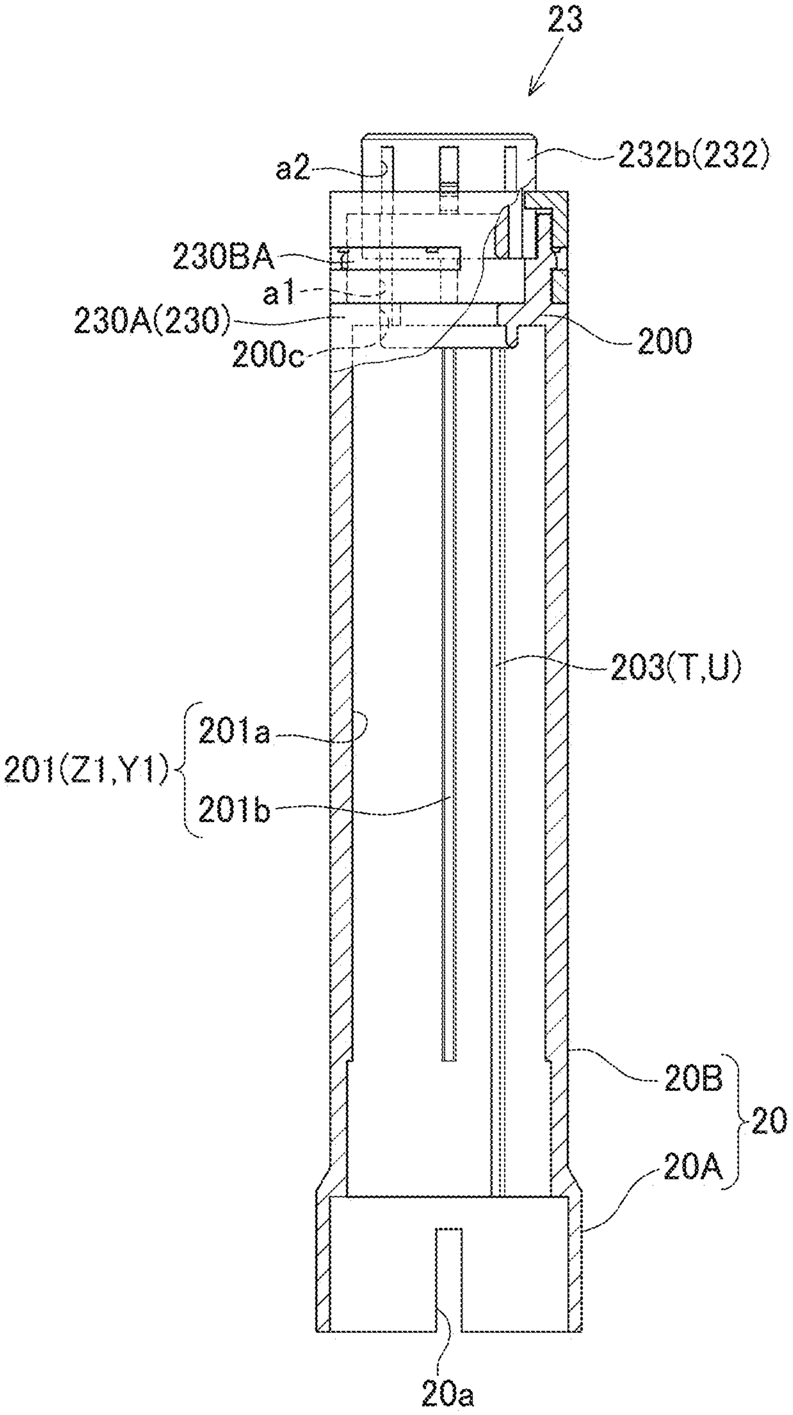
FIG. 20 is a cross-sectional view of a plunger accommodating portion of an injection device according to a second embodiment.

As shown in FIG. 20, a plunger accommodating portion 20 of the second embodiment includes a distal end accommodating portion 20A and an accommodating body portion 20B disposed on a proximal end side relative to the distal end accommodating portion 20A. In the plunger accommodating portion 20 of the second embodiment, the through hole 202 penetrating in the radial direction is not formed.

The distal end accommodating portion 20A accommodates a proximal end portion of a barrel accommodating portion 21 and a partition portion 22. The distal end accommodating portion 20A is disposed on a distal end side of the plunger accommodating portion 20. Further, the distal end accommodating portion 20A is formed in a tubular shape (specifically, a cylindrical shape). As shown in FIG. 20, the distal end accommodating portion 20A includes an axial cut-out portion 20*a* that is continuous from the distal end to the proximal end side and penetrates the circumferential surface. The axial cut-out portion 20*a* of the second embodiment includes a pair of axial cut-out portions provided so as to face each other in the radial direction.

The accommodating body portion 20B accommodates a plunger urging portion A and an engaging member C. The accommodating body portion 20B is formed in a tubular shape (specifically, a cylindrical shape). The accommodating body portion 20B is continuously provided with the proximal end of the distal end accommodating portion 20A. Because of this, in the plunger accommodating portion 20, the accommodating body portion 20B is disposed on the proximal end side relative to the distal end accommodating portion 20A. Further, the accommodating body portion 20B is formed longer than the distal end accommodating portion 20A in the direction of the central axis. Further, the accommodating body portion 20B of the second embodiment has an inner diameter and an outer diameter smaller than those of the distal end accommodating portion 20A. Because of this, the plunger accommodating portion 20 is formed such that the inner diameter and the outer diameter on the distal end side are larger than those on the proximal end side. Further, a distal end of the accommodating body portion 20B is provided in the plunger accommodating portion 20 as a step of the inner diameter difference between the distal end accommodating portion 20A and the accommodating body portion 20B.

An urging stand portion 200 is provided on the proximal end side of the accommodating body portion 20B. As shown in FIG. 20, the urging stand portion 200 of the second embodiment is provided with an urging attachment portion 200*c* configured to attach one end of the plunger urging portion A accommodated in the accommodating body portion 20B. The urging attachment portion 200*c* of the second embodiment is formed as an insertion through-hole 200*c* that penetrates the urging stand portion 200 in the direction of the central axis such that one end of the plunger urging portion A is inserted therethrough.

The plunger accommodating portion 20 includes a holding projection portion 201 (specifically, including a first holding projection portion 201*a* and a second holding projection portion 201*b*) as an engaging and holding mechanism Y1 that holds an engaging member C so as not to rotate with respect to the plunger accommodating portion 20. In the second embodiment, the holding projection portion 201 is formed in the accommodating body portion 20B as shown in FIG. 20. The holding projection portion 201 is continuously formed from the proximal end toward the distal end side, of the accommodating body portion 20B. Because of this, the holding projection portion 201 is fitted into a holding recess portion C4 which will be described below, and thus the holding projection portion 201 guides the engaging member C in the plunger accommodating portion 20 in the direction of the central axis. Further, when the holding projection portion 201 is fitted into the holding recess portion C4, the engaging member C is restricted from rotating, and a rotation by the plunger urging portion A is restricted.

Unlike the first embodiment, the distal end of the holding projection portion 201 of the second embodiment is provided in the plunger accommodating portion 20 on the proximal end side relative to the distal end of the accommodating body portion 20B formed as the step. Therefore, the distal end side of the accommodating body portion 20B is formed as a flat surface relative to the distal end of the holding projection portion 201. In the second embodiment, a distance from the distal end of the holding projection portion 201 to the distal end of the accommodating body portion 20B is equal to the distance between the urging receiving portion C2 and the urging engaging portion C3 of the engaging member C. In the second embodiment, as shown in FIG. 20, a distal end of the first holding projection portion 201*a* and a distal end of the second holding projection portion 201*b* are disposed as the same position in the direction of the central axis.

The plunger accommodating portion 20 of the second embodiment includes an engagement releasing mechanism Z1 that releases the engagement between the plunger 12 and the engaging member C. The plunger accommodating portion 20 of the second embodiment includes a rotary engaged portion 201 as the engagement releasing mechanism Z1. Specifically, the accommodating body portion 20B includes the rotary engaged portion 201. In the second embodiment, the holding projection portion 201 functions as the rotary engaged portion 201.

The plunger accommodating portion 20 includes a rotation allowance mechanism T that allows relative rotation of the plunger accommodating portion 20 and the engaging member C around the central axis. The accommodating body portion 20B of the second embodiment includes an accommodating projection portion 203 as the rotation allowance mechanism T. The accommodating projection portion 203 continuously extends from the proximal end to the distal end of the accommodating body portion 20B as shown in FIG. 20. Because of this, the accommodating projection portion 203 is disposed in the accommodating body portion 20B on the distal end side relative to the holding projection portion 201. The accommodating projection portion 203 of the second embodiment includes a pair of accommodating projection portions formed to face each other in the radial direction in the accommodating body portion 20B having a tubular shape. Further, the accommodating projection portion 203 is disposed between the first holding projection portion 201*a* and the second holding projection portion 201*b*.

The accommodating body portion 20B includes a rotation stop mechanism U that stops the rotation of the plunger 12 and the engaging member C around the central axis. The accommodating body portion 20B of the second embodiment includes an engaging stopped portion 203 as the rotation stop mechanism U. The engaging stopped portion 203 is configured as an accommodating projection portion 203 protruding in the radially inward direction in the accommodating body portion 20B.

In the trigger portion 23 of the second embodiment, the trigger attaching portion 230 and the trigger body portion 232 are different in configuration from those of the first embodiment. Specifically, the trigger attaching portion 230 of the second embodiment is formed with an urging attachment portion 200*c* (specifically, an insertion through-hole 200*c*) configured to attach one end of the plunger urging portion A to the proximal end portion 230A as shown in FIG. 20. Further, the circular cylinder body portion 230BA of the second embodiment is formed with a one-side guide portion a1 that communicates with the urging attachment portion 200*c*. In the second embodiment, the one-side guide portion a1 is formed along one end of the plunger urging portion A inserted through the insertion through-hole 200*c* such that the inside of the circular cylinder body portion 230BA is recessed.

The trigger body portion 232 of the second embodiment is formed with an other-side guide portion a2 along which one end of the plunger urging portion A is aligned with an outer skirt portion 232*b*. The other-side guide portion a2 is formed such that the outer periphery of the outer skirt portion 232*b* is recessed. Further, the other-side guide portion a2 is continuously formed from the distal end side to the proximal end side of the outer skirt portion 232*b*. As shown in FIG. 20, in the second embodiment, when the lock of the trigger portion 23 is released, the other-side guide portion a2 and the one-side guide portion a1 are disposed at the same position in the circumferential direction, and communicate with each other in the direction of the central axis. Then, when the trigger body portion 232 is pushed, the other-side guide portion a2 overlaps with the one-side guide portion a1.

Figure 22:
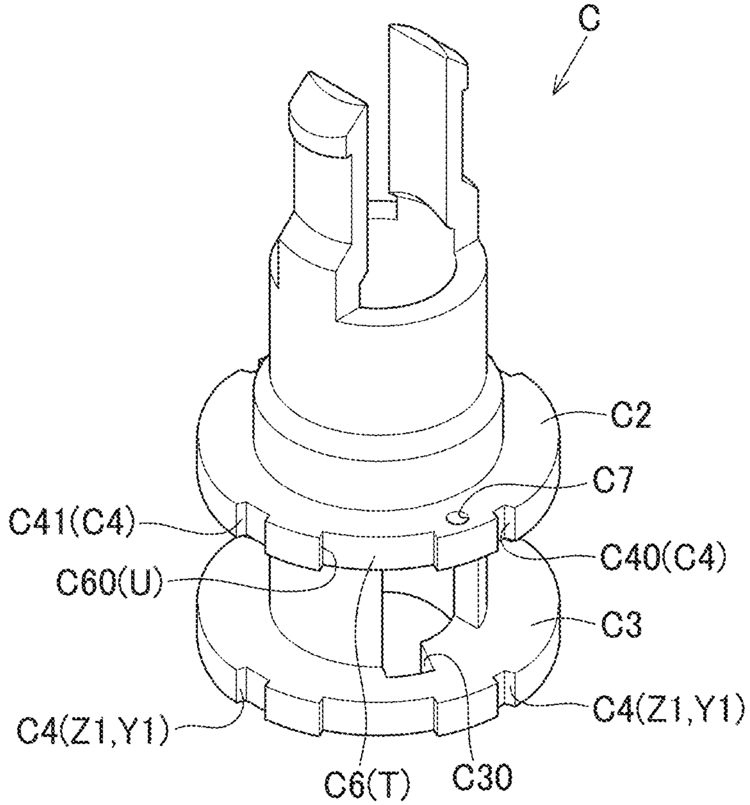
FIG. 22 is a perspective view of an engaging member according to the embodiment.

The plunger urging portion A of the second embodiment is configured as a torsion spring that extends and contracts in the direction of the central axis and accumulates a force (circumferential urging force) that rotates around the central axis. The plunger urging portion A forms the engagement releasing mechanism Z1. Because of this, the engagement releasing mechanism Z1 rotates the engaging member C around the central axis using the circumferential urging force of the plunger urging portion A. One end of the plunger urging portion A is attached to the urging attachment portion 200*c* provided in the plunger accommodating portion 20 as shown in FIG. 20. Further, the other end of the plunger urging portion A is attached to an urging attachment portion C7 provided in the engaging member C as shown in FIG. 22. Because of this, the plunger urging portion A extends from the compressed state to move the engaging member C. Further, the plunger urging portion A configured as the torsion spring is configured to rotate the engaging member C around the central axis by the circumferential urging force due to the torsion. Therefore, the plunger urging portion A is configured to urge the engaging member C in the direction in which the engaging member C rotates around the central axis. The plunger urging portion A of the second embodiment rotates when the fitting between the holding projection portion 201 and the holding recess portion C4 is released and the rotation restriction by the engaging and holding mechanism Y1 is released.

Figure 21:
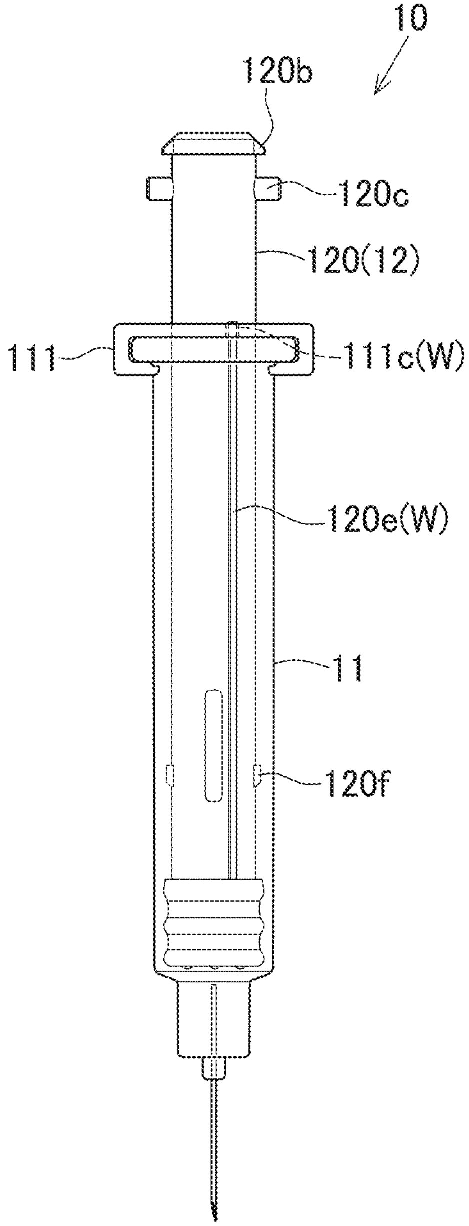
FIG. 21 is a side view of a syringe according to the embodiment.

The syringe 10 of the second embodiment is different from that of the first embodiment in that the engagement releasing mechanism Z1 is not provided. Specifically, as shown in FIG. 21, the rod 120 is not provided with the second branch portion 120*d* as a rotary engaging portion in the second embodiment. Further, the cover portion 111 is not provided with a rotary engaged portion. Because of this, an upper surface of the cover portion 111 of the second embodiment is formed as a flat surface.

Further, an axial movement protrusion portion 120*e* of the second embodiment is formed longer than that of the first embodiment on the proximal end side of the rod 120. In other words, as shown in FIG. 21, the axial movement protrusion portion 120*e* of the second embodiment is set to a length so as not to fall off from the axial movement groove portion 111*c* of the cover portion 111 when the plunger 12 inserted into the barrel 11 reaches the distal end (end point) of the barrel 11. Because of this, the rod 120 is prevented from rotating around the central axis in the second embodiment.

The engaging member C of the second embodiment is provided with the urging attachment portion C7 configured to attach the other end of the plunger urging portion A. Specifically, as shown in FIG. 22, an insertion hole C7 as the urging attachment portion C7 is formed in the urging receiving portion C2 to be used to insert the other end of the plunger urging portion A. Therefore, in the second embodiment, the engaging member C can rotate around the central axis by the circumferential urging force of the plunger urging portion A. The urging attachment portion C7 of the second embodiment is provided between a holding recess portion (specifically, a first holding recess portion C40) and an engaging recess portion C6 in a circumferential direction of the urging receiving portion C2 having an outer flange shape. Because of this, in the second embodiment, when the engaging member C and the plunger urging portion A are accommodated in the plunger accommodating portion 20, one end of the plunger urging portion A is attached to the urging attachment portion 200*c* and the other end of the plunger urging portion A is inserted into the insertion hole C7. The engaging member C advances toward the proximal end side of the plunger accommodating portion 20 in a state where torque is applied to the plunger urging portion A, and thus the plunger urging portion A is compressed.

The engaging member C of the second embodiment includes a holding recess portion C4 as an engaging and holding mechanism Y1. The holding recess portion C4 is fitted into the holding projection portion 201 when the engaging member C is accommodated in the plunger accommodating portion 20. Specifically, in the second embodiment, the holding recess portion C4 is formed such that circumferential surfaces of the urging receiving portion C2 and the urging engaging portion C3 are recessed as shown in FIG. 22. The holding recess portion C4 is formed to have a recess width that can be fitted with the holding projection portion 201. Because of this, when the engaging member C is accommodated in the plunger accommodating portion 20, the holding recess portion C4 is fitted with the holding projection portion 201, and thus the engaging member C is restricted from rotating in the direction of the central axis. In the second embodiment, the engaging member C moves in the direction of the central axis while keeping the holding recess portion C4 along the holding projection portion 201. Thus, the engaging member C is guided in the direction of the central axis in the plunger accommodating portion 20.

The engaging member C of the second embodiment includes rotary engaging portions C4 as engagement releasing mechanisms Z1. Specifically, as shown in FIG. 22, the engaging member C of the second embodiment is formed with holding recess portions C4 as the rotary engaging portions C4 in the urging receiving portion C2 and the urging engaging portion C3. When the holding recess portions C4 are fitted into the holding projection portion 201, the rotary engaging portions C4 are engaged with the rotary engaged portion 201. Here, the holding projection portion 201 of the second embodiment is provided on the proximal end side relative to the distal end of the accommodating body portion 20B. Because of this, the distal end side of the holding projection portion 201 is formed as a flat surface relative to the distal end thereof. In the engaging member C of the second embodiment, a distance between the urging receiving portion C2 and the urging engaging portion C3 is equal to or smaller than the distance from the distal end of the holding projection portion 201 to the accommodating body portion 20B. Therefore, when the engaging member C moves in the plunger accommodating portion 20 and the holding recess portion C4 is disposed on the distal end side relative to the distal end of the holding projection portion 201, the engagement between the rotary engaging portion C4 and the rotary engaged portion 201 is released.

The engaging member C of the second embodiment includes the rotation allowance mechanism T that allows relative rotation of the plunger accommodating portion 20 and the engaging member C around the central axis. Specifically, as shown in FIG. 22, the engaging member C of the second embodiment includes the engaging recess portion C6 as the rotation allowance mechanism T. The engaging recess portion C6 is provided so as to be recessed in the circumferential surfaces of the urging receiving portion C2 and the urging engaging portion C3. Further, the engaging recess portion C6 is formed larger in a width direction than the accommodating projection portion 203. Because of this, in the second embodiment, when the engaging member C is accommodated in the plunger accommodating portion 20, the engaging recess portion C6 fits (loosely fits) the accommodating projection portion 203 in itself. Therefore, the engaging recess portion C6 and the accommodating projection portion 203 move relative to each other around the central axis, and thus the plunger accommodating portion 20 and the engaging member C rotate relative to each other around the central axis. In the second embodiment, the engaging recess portion C6 moves around the central axis by the urging force in the circumferential direction of the plunger urging portion A. Therefore, the engaging member C rotates around the central axis. The engaging recess portions C6 of the second embodiment are provided between the first holding recess portion C40 and the second holding recess portion C41 on the circumferential surfaces of the urging receiving portion C2 and the urging engaging portion C3 having a circular shape in the direction of the central axis. Further, the engaging recess portion C6 includes two engaging recess portions C6 provided in each of the urging receiving portion C2 and the urging engaging portion C3.

Further, the engaging member C of the second embodiment includes the rotation stop mechanism U that stops the rotation of the plunger 12 and the engaging member C around the central axis. Specifically, as shown in FIG. 22, the engaging member C includes an engaging stop portion C60 as the rotation stop mechanism U. The engaging stop portions C60 of the second embodiment are provided on edges in the circumferential direction of the engaging recess portions C6 provided so as to be recessed on the circumferential surfaces of the urging receiving portion C2 and the urging engaging portion C3. Because of this, when the engaging recess portion C6 and the accommodating projection portion 203 move relative to each other around the central axis, the engaging stop portion C60 abuts on the accommodating projection portion 203 to stop the rotation of the plunger accommodating portion 20 and the engaging member C around the central axis.

Subsequently, a method of using the injection device 1 of the second embodiment will be described. In describing the method of using the injection device 1 of the second embodiment, functions of components different from those of the first embodiment will be described in detail. Because of this, the description will be made for the operation and subsequent thereto, after the cap of the housing is removed in the injection device 1 in the initial state, the lock is released to push the trigger portion 23 toward the plunger accommodating portion 20.

In the second embodiment, when the lock of the trigger portion 23 is released, the other-side guide portion a2 provided in the trigger body portion 232 is aligned in the circumferential direction with the one-side guide portion a1 provided in the circular cylinder body portion 230BA.

Further, the other-side guide portion a2 communicates with the one-side guide portion a1 in the direction of the central axis. The other-side guide portion a2 overlaps with the other-side guide portion a2 by a pushing operation of the trigger body portion 232. Therefore, the engagement between the trigger portion 23 and the engaging member C is released.

When the engagement between the trigger portion 23 and the engaging member C is released, the urging of the plunger urging portion A held in the compressed state on the proximal end side of the plunger accommodating portion 20 is released. In the second embodiment, the trigger portion 23 moves from an urging force holding position, at which the urging force of the plunger urging portion A is held so as not to be released, to an urging force releasing position at which the urging force of the plunger urging portion A is released. Then, when the plunger urging portion A is urged, the urging receiving portion C2 is pushed, and the engaging member C and the syringe 10 move to the distal end side of the plunger accommodating portion 20. Here, one end of the plunger urging portion A of the second embodiment is attached to the urging attachment portion 200*c* formed on the plunger accommodating portion 20. Further, the other end of the plunger urging portion A is attached to the urging attachment portion C7 provided on the engaging member C. Then, in the state where the engaging member C is accommodated on the proximal end side of the plunger accommodating portion 20, the engaging and holding mechanism Y1 is formed by the fitting of the holding recess portion C4 and the holding projection portion 201. Because of this, the engaging and holding mechanism Y1 restricts the engaging member C from rotating around the central axis with respect to the plunger accommodating portion 20. Further, the engaging and holding mechanism Y1 of the second embodiment restricts the rotation of the engaging member C to maintain the urging force in the circumferential direction of the plunger urging portion A. Therefore, the plunger urging portion A having the other end attached to the engaging member C does not rotate around the central axis in the state of being released from compression, extends toward the distal end side in the direction of the central axis, and pushes the engaging member C and the syringe 10 toward the distal end side. Therefore, the engaging member C advances toward the distal end side in the direction of the central axis until the fitting between the holding projection portion 201 and the holding recess portion C4 is released. In the second embodiment, the engaging recess portion C6 and the accommodating projection portion 203 are fitted to each other.

As the engaging member C advances toward the distal end side of the plunger accommodating portion 20, the cover portion 111 moves in the direction of the central axis while compressing the barrel urging portion B until the bottom surface abuts on the barrel receiving portion 210*a*. At this time, the holding recess portion 111*b* of the cover portion 111 moves along the holding projection portion of the barrel accommodating portion 21 as in the first embodiment. Because of this, the barrel 11 moves toward the distal end side in the direction of the central axis without rotating around the central axis. Thereafter, as shown in FIG. 23, the barrel 11 moves from a first position to a second position, and the injection needle 13 protrudes from the barrel accommodating portion 21.

Figure 23:
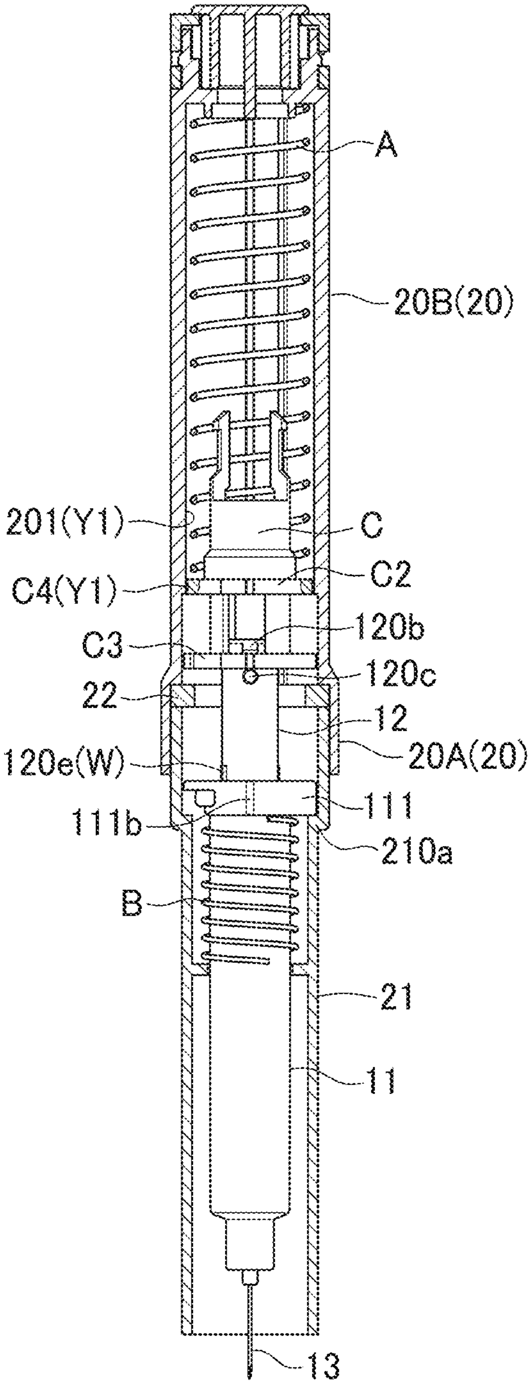
FIG. 23 is a front view showing the injection device of the embodiment, in which a housing is shown in a cross section and engagement between a rotary engaging portion and a rotary engaged portion is in a state immediately before being released.

As shown in FIG. 23, when the cover portion 111 abuts on the barrel receiving portion 210*a*, the movement of the barrel 11 toward the distal end side is stopped. When the movement of the barrel 11 is stopped, the pushing due to the urging of the plunger urging portion A is applied to the engaging member C and the plunger 12. Because of this, the engaging member C and the plunger 12 move toward the distal end side in the direction of the central axis. Here, the plunger 12 of the second embodiment moves in the barrel 11 while pushing the drug solution in the barrel 11 out of the barrel 11 from the start point toward the end point (distal end of the barrel). At this time, the axial movement protrusion portion 120*e* provided on the rod 120 is located along the axial movement groove portion 111*c*. Because of this, the plunger 12 advancing in the barrel 11 does not rotate around the central axis. Specifically, as shown in FIG. 21, the axial movement protrusion portion 120*e* of the second embodiment is set to the length so as not to fall off from the axial movement groove portion 111*c* of the cover portion 111 when the plunger 12 reaches the distal end of the barrel 11. Because of this, in the second embodiment, even when the plunger 12 reaches the distal end of the barrel 11, since the axial movement protrusion portion 120*e* does not fall off from the axial movement groove portion 111*c*, the restriction by the rotation restriction portion W is not released. Therefore, in the second embodiment, the plunger 12, which has moved in the direction of the central axis, does not rotate around the central axis.

Figure 24:
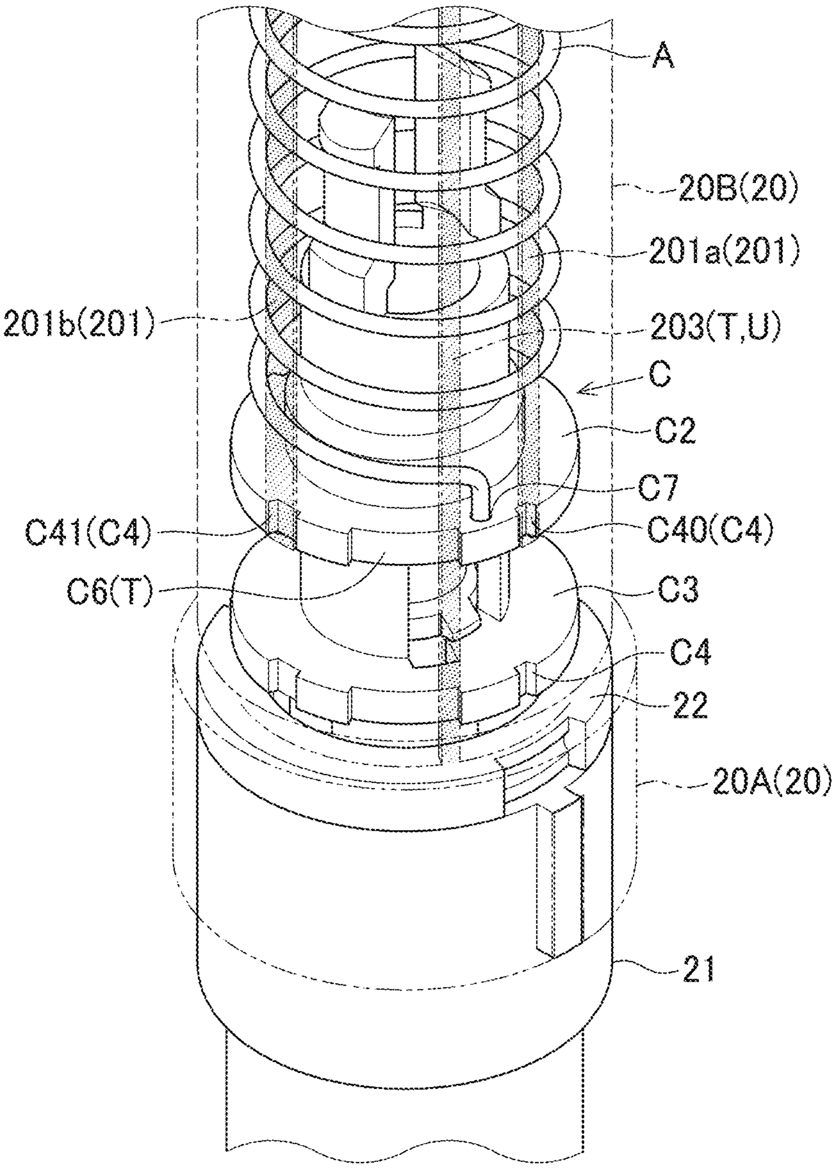
FIG. 24 is a detailed view showing a state immediately before the engagement between the rotary engaging portion and the rotary engaged portion is released.

Due to the urging of the plunger urging portion A, the engaging member C advances in the accommodating body portion 20B while the holding recess portion C4 is located along the holding projection portion 201. In the second embodiment, as shown in FIG. 23, the plunger urging portion A extends, and thus the engaging member C moves toward the distal end side from the proximal end side of the plunger accommodating portion 20. In the second embodiment, as shown in FIG. 24, the engaging recess portion C6 is located along the accommodating projection portion 203.

When the engaging member C moves to the distal end side of the plunger accommodating portion 20, the fitting between the holding projection portion 201 and the holding recess portion C4 is released. Specifically, as shown in FIG. 24, in the second embodiment, first, the fitting between the holding recess portion C4 provided in the urging engaging portion C3 and the holding projection portion 201 of the plunger accommodating portion 20 is released. Thereafter, due to the urging of the plunger urging portion A, the engaging member C moves toward the distal end side of the plunger accommodating portion 20 in the direction of the central axis while the holding recess portion C4 provided in the urging receiving portion C2 is located along the holding projection portion 201.

Figure 25:
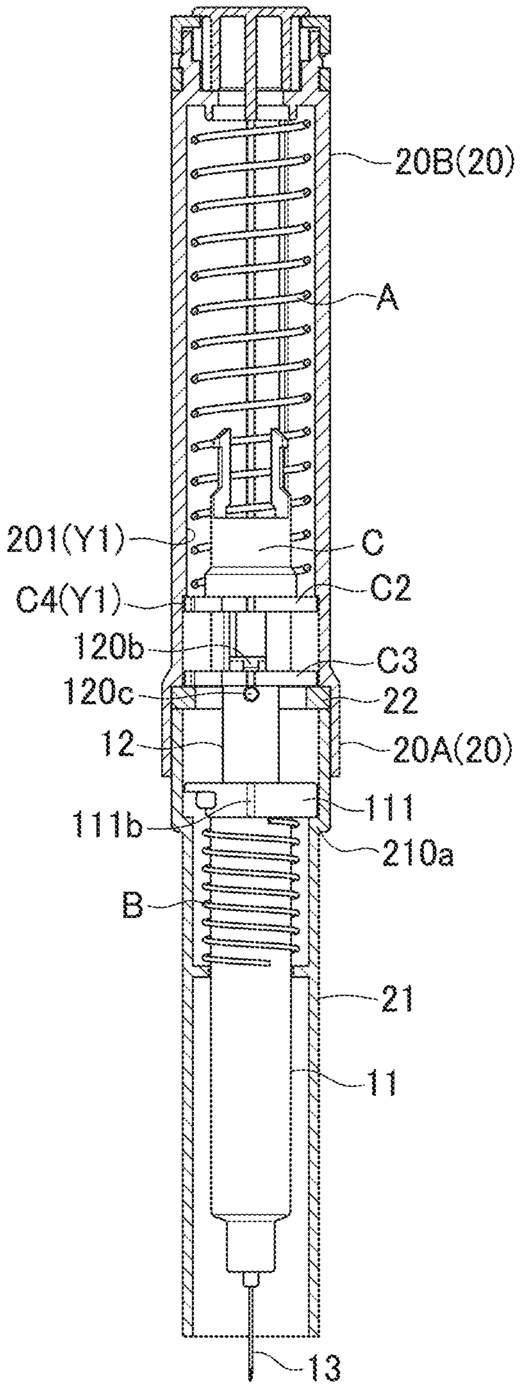
FIG. 25 is a front view of the injection device according to the embodiment, in which a housing is shown in a cross section and the engagement between the rotary engaging portion and the rotary engaged portion is in a state of being released.
Figure 26:
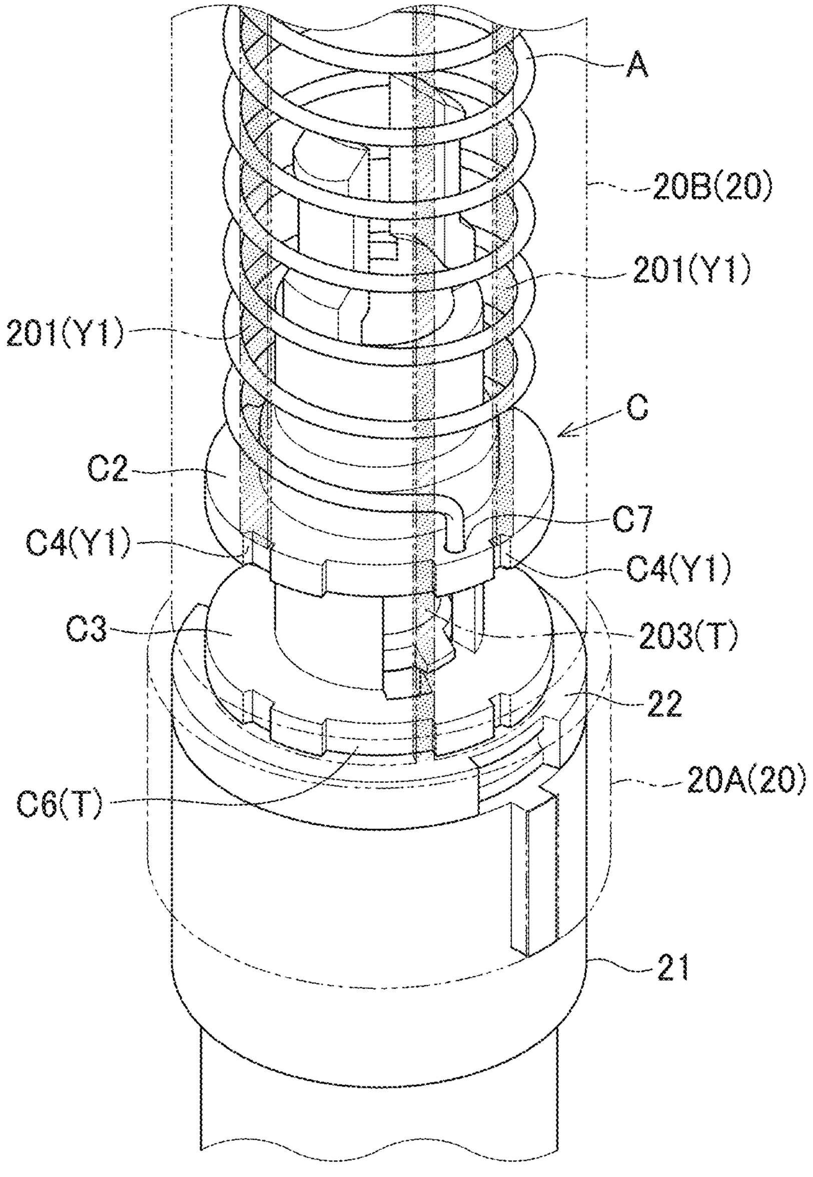
FIG. 26 is a detailed view showing a state where the engagement between the rotary engaging portion and the rotary engaged portion is released.

Due to the urging of the plunger urging portion A, the engaging member C in the state shown in FIG. 23 moves toward the distal end side of the plunger accommodating portion 20 in the direction of the central axis. The engaging member C in the state shown in FIG. 25 is urged and fixed when the urging engaging portion C3 moves to the position close to the partition portion 22. At this time, as shown in FIG. 26, the fitting between the holding recess portion C4 formed in the urging receiving portion C2 and the holding projection portion 201 is released. Therefore, the restriction by the engaging and holding mechanism Y1, which holds the engaging member C so as not to rotate with respect to the plunger accommodating portion 20, is released. In the second embodiment, when the urging engaging portion C3 moves to the position close to the partition portion 22, the plunger 12 reaches the end point (distal end of the barrel 11).

When the restriction by the engaging and holding mechanism Y1 is released, the urging force in the circumferential direction of the plunger urging portion A is released. In the second embodiment, as shown in FIGS. 23 and 24, one end of the plunger urging portion A is attached to the urging attachment portion C7 of the engaging member C. In the second embodiment, the plunger accommodating portion 20 and the engaging member C include the rotation allowance mechanism T. Specifically, the accommodating body portion 20B includes the accommodating projection portion 203, and the engaging member C includes the engaging recess portion C6. Then, in the second embodiment, the engaging recess portion C6 and the accommodating projection portion 203 are fitted (loosely fitted) to each other. Because of this, in the second embodiment, the engaging recess portion C6 moves relative to the accommodating projection portion 203 around the central axis with the urging force in the circumferential direction of the plunger urging portion A. In other words, in the second embodiment, the engaging member C rotates to change from the state of FIG. 26 to the state of FIG. 28 using the urging force in the circumferential direction of the plunger urging portion A configured as the torsion spring.

Figure 28:
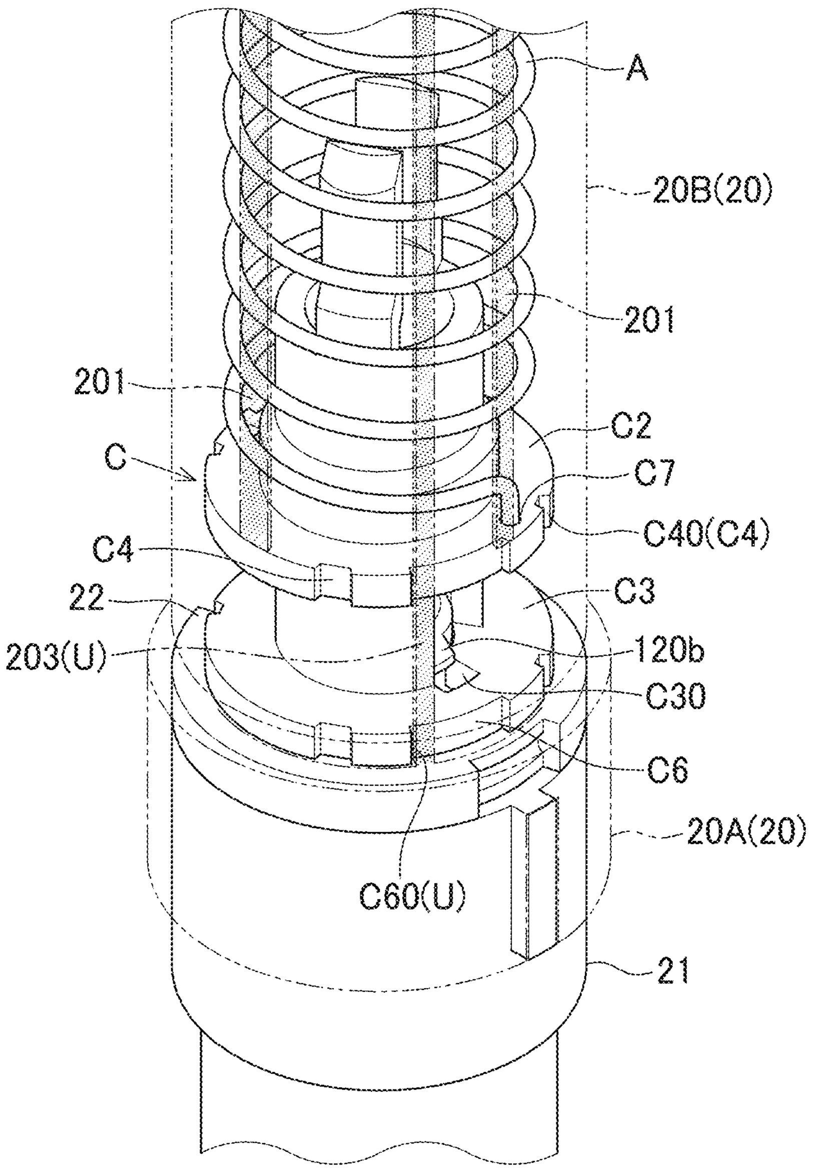
FIG. 28 is a detailed view showing a state where the engaging member rotates around the central axis.

Thereafter, the rotation of the engaging member C around the central axis is stopped by the rotation stop mechanism U. Specifically, in the second embodiment, as shown in FIG. 28, the engaging member C rotates around the central axis, and thus the engaging stop portion C60 provided at the edge in the circumferential direction of the engaging recess portion C6 abuts on the accommodating projection portion 203. Thus, the rotation of the engaging member C around the central axis is stopped. In the second embodiment, when the plunger accommodating portion 20 and the engaging member C around the central axis is stopped as shown in FIG. 28, the holding projection portion 201 and the holding recess portion C4 are disposed at different positions in the circumferential direction. Because of this, the engaging member C is fixed so as not to move to the proximal end side of the plunger accommodating portion 20.

Figure 27:
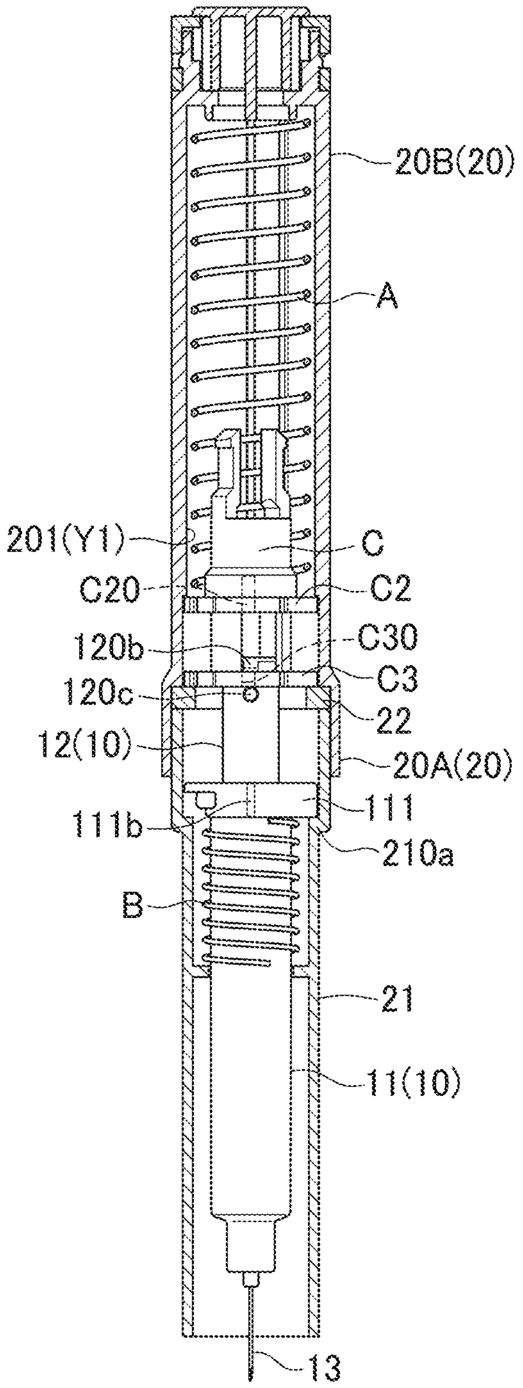
FIG. 27 is a front view of the injection device according to the embodiment, in which a housing is shown in a cross section and the engaging member rotates around the central axis.

Due to the rotation of the engaging member C, the release hole C30 also rotates. In the second embodiment, when the engaging stop portion C60 and the accommodating projection portion 203 abut on each other and the rotation of the engaging member C around the central axis is stopped, the release hole C30 is disposed at the position that coincides with the first branch portion 120*c* and the pin portion 120*b* in the circumferential direction, as shown in FIGS. 27 and 28. Therefore, the engagement between the urging engaging portion C3 and the urging engaged portion 120*c* is released, and the engagement between the plunger 12 and the engaging member C is released.

In other words, the engagement releasing mechanism Z1 of the second embodiment rotates the engaging member C around the central axial with respect to the plunger 12 with the urging force in the circumferential direction of the plunger urging portion A when the engagement between the rotary engaged portion 201 and the rotary engaging portion C4 is released, whereby the engagement between the plunger 12 and the engaging member C is released.

When the engagement between the first branch portion 120*c* and the urging engaging portion C3 is released, the urging of the plunger urging portion A against the syringe 10 is released. Because of this, the barrel urging portion B compressed by the urging of the plunger urging portion A is released, and thereby the syringe 10 is pushed toward the proximal end side. Therefore, the barrel 11 and the plunger 12 move to the proximal end side, and the pin portion 120*b* is fitted into the rotation-prevention fitted portion C20. Therefore, the barrel 11 can be moved from the second position to the first position to accommodate the injection needle 13 in the housing.

In the injection device 1 of the second embodiment as described above, the plunger urging portion A is configured to urge the engaging member C in the direction in which the engaging member C rotates around the central axis, and the engagement releasing mechanism Z1 is configured to release the engagement between the plunger 12 and the engaging member C by rotating the engaging member C so as not to rotate around the central axis with respect to the plunger 12 by the urging force in the circumferential direction of the plunger urging portion A. Because of this, the engaging member C rotates around the central axis, and thus the engagement between the plunger 12 and the engaging member C is released, whereby the urging of the plunger urging portion A toward the plunger 12 is released, for example. Therefore, the syringe 10 is urged to the other side in the direction of the central axis by the urging of the barrel urging portion B, whereby the injection needle 13 can be pulled into the housing.

In the second embodiment, the plunger urging portion A is the torsion spring, and is configured to rotate the engaging member C by the urging force in the circumferential direction of the torsion spring. Because of this, according to the above configuration, the engaging member C rotates due to the urging force in the circumferential direction of the plunger urging portion A that is the torsion spring, and thus the engagement between the plunger 12 and the engaging member C can be released.

In the second embodiment, the engagement releasing mechanism Z1 includes the rotary engaging portion C4 provided on the engaging member C and the rotary engaged portion 201 provided on the plunger accommodating portion 20, the rotary engaging portion C4 and the rotary engaged portion 201 are engaged with each other, the plunger 12 moves from the start point to the end point, and the engagement between the rotary engaging portion C4 and the rotary engaged portion 201 is released, whereby the plunger 12 and the engaging member C rotate relative to each other around the central axis, and the engagement between the plunger 12 and the engaging member C is released. Because of this, since the disengagement position between the rotary engaging portion C4 and the rotary engaged portion 201 can be set according to the moving position of the plunger 12 with respect to the barrel 11, the engagement between the rotary engaging portion C4 and the rotary engaged portion 201 can be released according to the end point of the movement of the plunger 12, for example.

In the second embodiment, the holding projection portion 201 and the holding recess portion C4 are fitted to each other, the plunger 12 moves from the start point to the end point, and the fitting between the holding projection portion 201 and the holding recess portion C4 is released, whereby the engaging member C relatively rotates around the central axis, and the engagement between the plunger 12 and the engaging member C is released. Because of this, when the plunger 12 reaches the end point (distal end of the barrel 11), the engaging member C can rotate relative to the plunger 12.

In the injection device 1 of the second embodiment, when the plunger 12 moves to the end point, the engagement between the holding recess portion C4 and the holding projection portion 201 is released, the engaging member C rotates around the central axis, and the engagement between the plunger 12 and the engaging member C is released. According to the above configuration, for example, when the plunger 12 moves to the distal end of the barrel 11 as a terminal, the engagement between the holding recess portion C4 and the holding projection portion 201 is released, whereby when the discharging of the drug solution in the barrel 11 is completed, the syringe 10 can be urged to the other side in the direction of the central axis by the urging of the barrel urging portion B and the injection needle 13 can be pulled into the housing 2.

Further, the injection device 1 of the second embodiment includes the rotation stop mechanism U that stops the relative rotation of the plunger 12 and the engaging member C around the central axis, the rotation stop mechanism U includes the engaging stop portion C60 provided in the engaging member C and the engaging stopped portion 203 provided in the plunger accommodating portion 20, and the engaging stop portion C60 and the engaging stopped portion 203 are engaged with each other, whereby the relative rotation of the plunger 12 and the engaging member C around the central axis is stopped. Because of this, the relative rotation of the plunger 12 and the engaging member C around the central axis is stopped, and the plunger 12 and the engaging member C can be prevented from continuously rotating relative to each other around the central axis in the plunger accommodating portion 20.

In the injection device 1 of the second embodiment, the engaging member C rotates around the central axis, and when the rotation is stopped by the rotation stop mechanism U, the holding projection portion 201 and the holding recess portion C4 are disposed at different positions in the circumferential direction. Because of this, in the second embodiment, after rotating around the central axis, the engaging member C can be prevented from moving to the proximal end side of the plunger urging portion A.

In the second embodiment, the case has been described in which the rotary engaging portion is the holding recess portion C4 and the rotary engaged portion is the holding projection portion 201. However, the present invention is not limited thereto, and the rotary engaging portion can be the holding projection portion 201 and the rotary engaged portion can be the holding recess portion C4.

In the second embodiment, the case has been described in which the engaging member C rotates around the central axis with respect to the plunger 12. However, the present invention includes a case of rotating the plunger 12 or a case of rotating both the plunger 12 and the engaging member C in opposite directions without being limited thereto.

Figure 29:
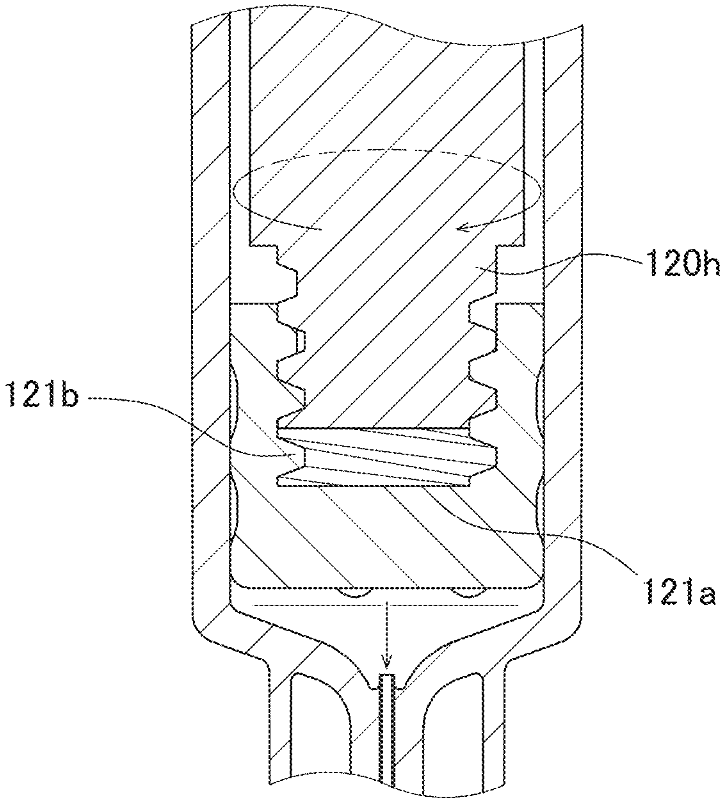
FIG. 29 is a partially enlarged cross-sectional view of a syringe according to a modified example of the injection device.

In the first and second embodiments, the case has been described in which the distal end protrusion portion 120*h* of the rod 120 is inserted into the coupling hole 121*a* of the piston 121 and the piston 121 and the rod are coupled with each other. However, the present invention is not limited thereto, and the piston 121 and the rod 120 can be coupled with each other in a manner that a male screw or a female screw as a screw 121*b* formed on the piston is screwed with a female screw or a male screw as a screw 120*h* formed on the rod, as shown in FIG. 29. When the engagement releasing mechanism is configured to rotate the rod, the direction of the rotation of the rod can also be set to a direction in which the screw is loosened. The screw is loosened by the rotation of the rod when the plunger moves to a position immediately before the distal end of the barrel 11, and the piston can be further pushed toward the end of the barrel 11 on the injection needle 13 side. Thus, the drug solution can be prevented from remaining in the barrel 11. Naturally, the rotation direction of the rod 120 can be a direction in which the screw is tightened. Further, it can be configured such that the distal end of the rod 120 abuts on the end surface of the piston 121 and thereby push the piston 121 into the barrel 11. In this case, the rod 120 can be configured not to include the distal end protrusion portion 120*h* at the distal end thereof. The piston 121 can be configured not to include the coupling hole 121*a*.

In the first and second embodiments, the case has been described in which the barrel 11 is urged by the barrel urging portion B and abuts on the partition portion 22 in the state where the injection needle 13 is pulled into the housing 2. However, the present invention is not limited thereto, and the barrel 11 can be configured not to abut on the partition portion 22. Further, the partition portion 22 may not be provided.

The barrel urging portion B and the plunger urging portion A are not limited to the spring, and can be rubber.

In the first embodiment, the urging receiving portion C2 and the urging engaging portion C3 of the engaging member C are separately provided, but the urging engaging portion C3 can also be used as the urging receiving portion C2. In the first embodiment, the first branch portion 120*c* and the second branch portion 120*d* are formed in a columnar shape, but can have other shapes. For example, the first branch portion 120*c* can be a prism or a fan-shaped plate centered on the central axis O. In the case of the fan-shaped plate, the release hole C30 is also preferably a fan-shaped hole. The second branch portion 120*d* can be an inclined surface corresponding to the inclined surface 111*aa* of the inclined portion 111*a*. Further, it can have a rib shape extending in the direction of the central axis O in which the first branch portion 120*c* and the second branch portion 120*d* are coupled with each other.

In the first and second embodiments, the case has been described in which the start point is at the position on the distal end side relative to the proximal end of the barrel and the end point is the distal end of the barrel. However, the present invention is not limited thereto, and the start point can be the proximal end of the barrel (proximal end portion of the body portion 110*b*), or the end point can be the proximal end side relative to the distal end of the barrel. In other words, as long as the start point is the proximal end side of the barrel and the end point is the distal end side, the start point can be set to the proximal end portion of the barrel, and the end point can be set to a position other than the distal end portion of the barrel.

It should be noted that the relative rotation between the plunger and the engaging member is not limited to the case of operating immediately before the end point as in the first embodiment, and the plunger and the engaging member can rotate relative to each other from the beginning of the movement of the plunger. In other words, the engagement between the plunger and the engaging member can be released by the relative rotation of the plunger and the engaging member around the central axis, and the end point can be a position where the movement from the start point of the plunger stops.

In the first and second embodiments, the trigger portion is configured to release the urging of the plunger urging portion by the pushing operation of the trigger portion. However, the present is not limited thereto. Examples of a predetermined operation of releasing the holding of the urging of the plunger urging portion can include an operation of pulling the trigger portion in the direction of the central axis or an operation of rotating the trigger portion around the central axis. In other words, the trigger portion can be configured to move between the urging force holding position at which the urging force of the plunger urging portion is not released and the urging force releasing position at which the urging of the plunger urging portion is released from the urging force holding position.

REFERENCE SIGNS LIST

1: Injection device
10: Syringe
11: Barrel
110: Barrel body
110*a*: Outer flange portion
110*b*: Body portion
111: Cover portion
111*a*: Inclined portion (rotary engaged portion)
111*aa*: Inclined surface
111*ab*: Horizontal surface
111*ac*: Vertical surface
111*b*: Holding recess portion
111*c*: Axial movement groove portion
111*e*: Insertion through-hole
12: Plunger
120: Rod
120*a*: Rod body
120*b*: Pin portion (rotation-prevention fitting portion)
120*c*: First branch portion (urging engaged portion)
120*d*: Second branch portion (rotary engaging portion)
120*e*: Axial movement protrusion portion
120*f*: Fall-off proof portion
120*h*: Distal end protrusion portion
120*h*: Screw
121: Piston
121*a*: Coupling hole
121*b*: Annular protrusion
121*b*: Screw
13: Injection needle
2: Housing
20: Plunger accommodating portion
20*a*: Axial cut-out portion
200: Urging stand portion
200*a*: Distal end side protrusion portion
200*b*: Insertion through-hole
201: Holding projection portion
201*a*: First holding projection portion
202: Through hole
21: Barrel accommodating portion
210: Large cylinder-side barrel accommodating portion
210*a*: Barrel receiving portion
210*b*: Holding projection portion
211: Small cylinder-side barrel accommodating portion
211*a*: Urging stand portion
22: Partition portion
220: Through hole
23: Trigger portion
230: Trigger attaching portion
230A: Proximal end portion
230B: Circular cylinder
230BA: Circular cylinder body portion
230BB: Lock step portion
230BC: Projection portion
230*a*: Hooking portion
230*bb*: Interlocking groove
231: Trigger lock operation portion
231*a*: Circular cylinder body portion
231*aa*: Rotating groove
231*b*: Inner flange portion
231*ba*: Interlocking projection portion
232: Trigger body portion
232*a*: Top plate portion
232*b*: Outer skirt portion
232*ba*: Release groove
232*c*: Inner skirt portion
232*d*: Flat plate portion
A: Plunger urging portion
B: Barrel urging portion
C: Engaging member
C1: Engaging body
C11: Opening passage
C2: Urging receiving portion
C20: Rotation-prevention fitted portion
C3: Urging engaging portion
C30: Release hole
C4: Holding recess portion
C4: Holding projection portion
C40: First holding recess portion
C41: Second holding recess portion
C5: Trigger locking portion
C50: Rib
K: Cap
K1: Needle cap holding portion
K2: Needle cap
O: Central axis
V: Lock mechanism portion
W: Rotation restriction portion
X: Rotation holding mechanism
Y: Reverse rotation prevention means
Y1: Engaging and holding mechanism
Y2: Reverse rotation prevention mechanism
Z1: Engagement releasing mechanism

The invention claimed is:

1. An injection device comprising:

a syringe including a barrel provided with an injection needle at a distal end thereof and a plunger inserted into the barrel so as to be capable of reciprocating between a proximal end side of the barrel as a start point and the injection needle as an end point;

a housing formed in a tubular shape to accommodate the syringe, the housing including a barrel accommodating portion formed on one side in a direction of a central axis and accommodating the barrel to be movable between a state where the injection needle is accommodated and a state where the injection needle protrudes from one side of the housing at a predetermined distance from the accommodated state to one side and a plunger accommodating portion formed on another side relative to the barrel accommodating portion and accommodating the plunger protruding from the proximal end side of the barrel;

a barrel urging portion provided in the barrel accommodating portion and urging the barrel from the one side to the other side of the housing;

an engaging member disposed in the plunger accommodating portion and configured to be retainably engaged with the plunger until the engagement between the plunger and the engaging member is released;

a plunger urging portion engaged with the engaging member and urging the plunger from the start point toward the end point;

a trigger portion configured to hold urging of the plunger urging portion so as not to release the urging in a state where the barrel accommodates the injection needle by the barrel urging portion and a state where the plunger resists against an urging force of the plunger urging portion and a distal end of the plunger is located at a position of the start point, and to release the holding by performing a predetermined operation, and an engagement releasing mechanism configured to release engagement between the plunger and the engaging member and to cause the plunger to be located at the end point in a manner that the plunger moves from the start point toward the end point by the urging force of the plunger urging portion to thereby cause the injection needle to protrude from the housing and the plunger and the engaging member rotate relative to each other around the central axis, wherein the engagement releasing mechanism includes a rotary engaging portion provided on the plunger and a rotary engaged portion provided on the barrel, wherein the plunger is configured to move from the start point toward the end point, the rotary engaging portion and the rotary engaged portion are engaged with each other, and the plunger is configured to rotate around the central axis to release the engagement between the plunger and the engaging member to thereby pull the injection needle into the housing, and the rotary engaging portion comprises a pair of rotary engaging portions provided in a direction orthogonal to the central axis.

2. The injection device according to claim 1, wherein when the plunger moves from the start point to a position immediately before the end point, the rotary engaging portion and the rotary engaged portion are engaged with each other, and thus the plunger rotates around the central axis to release the engagement between the plunger and the engaging member.

3. The injection device according to claim 1, wherein the barrel includes a barrel body filled with a drug solution and a cover portion attached to the barrel body, the cover portion is accommodated in the barrel accommodating portion so as not to rotate with the barrel accommodating portion, and the cover portion is provided with the rotary engaged portion.

4. An injection device comprising:

a syringe including a barrel provided with an injection needle at a distal end thereof and a plunger inserted into the barrel so as to be capable of reciprocating between a proximal end side of the barrel as a start point and the injection needle as an end point;

a housing formed in a tubular shape to accommodate the syringe, the housing including a barrel accommodating portion formed on one side in a direction of a central axis and accommodating the barrel to be movable between a state where the injection needle is accommodated and a state where the injection needle protrudes from one side of the housing at a predetermined distance from the accommodated state to one side and a plunger accommodating portion formed on another side relative to the barrel accommodating portion and accommodating the plunger protruding from the proximal end side of the barrel;

a barrel urging portion provided in the barrel accommodating portion and urging the barrel from the one side to the other side of the housing;

an engaging member disposed in the plunger accommodating portion and engaged with the plunger;

a plunger urging portion engaged with the engaging member and urging the plunger from the start point toward the end point;

a trigger portion configured to hold urging of the plunger urging portion so as not to release the urging in a state where the barrel accommodates the injection needle by the barrel urging portion and a state where the plunger resists against an urging force of the plunger urging portion and a distal end of the plunger is located at a position of the start point, and to release the holding by performing a predetermined operation, and an engagement releasing mechanism configured to release engagement between the plunger and the engaging member and to cause the plunger to be located at the end point in a manner that the plunger moves from the start point toward the end point by the urging force of the plunger urging portion to thereby cause the injection needle to protrude from the housing and the plunger and the engaging member rotate relative to each other around the central axis, wherein the plunger urging portion is configured to urge the engaging member in a direction in which the engaging member rotates around the central axis by circumferential urging force of the plunger urging portion, and the engagement releasing mechanism is configured to release the engagement between the plunger and the engaging member to thereby pull the injection needle into the housing by rotating the engaging member around the central axis with respect to the plunger by the circumferential urging force of the plunger urging portion.

5. The injection device according to claim 4, wherein the plunger accommodating portion includes an accommodating body portion, and a holding projection portion, a distal end of the holding projection portion is provided on the proximal end side of the barrel relative to a distal end of the accommodating body portion, the engaging member includes a holding recess portion that is fitted with the holding projection portion, when the engaging member is accommodated in the accommodating body portion, the holding recess portion is fitted with the holding projection portion, and thereby the engaging member is restricted from rotating around the central axis, and the plunger urging portion is a torsion spring, and is configured to rotate the engaging member by an urging force generated by twisting of the torsion spring.

* * * * *